US007387874B2

(12) United States Patent
Gocke et al.

(10) Patent No.: US 7,387,874 B2
(45) Date of Patent: *Jun. 17, 2008

(54) DETECTION OF EXTRACELLULAR TUMOR-ASSOCIATED NUCLEIC ACID IN BLOOD PLASMA OR SERUM USING NUCLEIC ACID AMPLIFICATION ASSAY

(75) Inventors: Christopher D. Gocke, Elliott City, MD (US); Michael Kopreski, Long Valley, NJ (US)

(73) Assignee: The Penn State Research Foundation, University Park, PA (US)

( * ) Notice: Subject to any disclaimer, the term of this patent is extended or adjusted under 35 U.S.C. 154(b) by 467 days.

This patent is subject to a terminal disclaimer.

(21) Appl. No.: 10/680,060

(22) Filed: Oct. 7, 2003

(65) Prior Publication Data

US 2005/0112581 A1 May 26, 2005

Related U.S. Application Data

(60) Division of application No. 10/298,816, filed on Nov. 18, 2002, now Pat. No. 6,939,675, which is a continuation of application No. 09/642,952, filed on Aug. 21, 2000, now Pat. No. 6,521,409, which is a continuation of application No. 08/818,058, filed on Mar. 14, 1997, now Pat. No. 6,156,504.

(60) Provisional application No. 60/028,180, filed on Oct. 15, 1996, provisional application No. 60/026,252, filed on Sep. 17, 1996, provisional application No. 60/013,497, filed on Mar. 15, 1996.

(51) Int. Cl.
| | |
|---|---|
| *C12Q 1/68* | (2006.01) |
| *C12P 19/34* | (2006.01) |
| *C07H 21/04* | (2006.01) |

(52) U.S. Cl. .................. 435/6; 536/24.33; 435/91.2
(58) Field of Classification Search ............ 435/6, 435/91.2; 536/23.1, 24.31, 24.33
See application file for complete search history.

(56) References Cited

U.S. PATENT DOCUMENTS

| | | | |
|---|---|---|---|
| 4,965,188 A | 10/1990 | Mullis | |
| 5,024,934 A | 6/1991 | Lee et al. | |
| 5,088,492 A | 2/1992 | Takayama et al. | |
| 5,182,377 A | 1/1993 | Manos | |
| 5,283,171 A | 2/1994 | Manos | |
| 5,496,699 A | 3/1996 | Sorenson | |
| 5,512,439 A | 4/1996 | Hornes | |
| 5,512,441 A * | 4/1996 | Ronai | 435/6 |
| 5,527,676 A | 6/1996 | Vogelstein | |
| 5,527,898 A | 6/1996 | Bauer | |
| 5,545,527 A | 8/1996 | Stevens et al. | |
| 5,639,871 A | 6/1997 | Bauer | |
| 5,648,212 A * | 7/1997 | Albertsen et al. | 435/6 |
| 5,705,627 A | 1/1998 | Manos | |
| 5,814,448 A | 9/1998 | Silverstein | |
| 5,952,170 A | 9/1999 | Stroun et al. | |
| RE36,713 E | 5/2000 | Vogelstein | |
| 6,090,566 A | 7/2000 | Vogelstein | |
| 6,156,504 A * | 12/2000 | Gocke et al. | 435/6 |
| 6,383,733 B1 | 5/2002 | Beug et al. | |
| 6,521,409 B1 * | 2/2003 | Gocke et al. | 435/6 |
| 6,630,301 B1 * | 10/2003 | Gocke et al. | 435/6 |

FOREIGN PATENT DOCUMENTS

| | | |
|---|---|---|
| WO | WO8900206 | 11/1989 |
| WO | WO 9322456 A1 * | 11/1993 |
| WO | WO 9513368 A1 * | 5/1995 |
| WO | WO9615139 | 5/1996 |
| WO | WO9516792 | 6/1996 |
| WO | WO9734015 | 9/1997 |

OTHER PUBLICATIONS

Moran et al. Utilization of sigmoidoscopy. Can Med Assoc J., vol. 150 (10), p. 1544, 1994.*
Runnebaum et al., Feb. 6-9, 1996, Abstract from Anti-Cancer Treatment, Sixth International Congress, p. 93.
LeJeune et al, 1993, Amphiregulin, Epidermal Growth Factor Receptor, and Estrogen Receptor Expression in Human Primary Breast Cancer, Cancer Research 53:3597-3602.
Urdea et al., 1994, Branched DNA Signal Amplification, Bio/Technology, 12: 927-928.
Chelly et al., 1989, Illegitimate transcription: Transcription of any gene in any cell type, PNAS 86: 2617-2621.
Aggarwal, et al., (Mar. 1975) "Cell-Surface-Associated Nucleic Acid in Tumorigenic Cells Made Visible with Platinum-Pyrimidien Complexes by Electron Microscopy." *Proc. Natl. Acad. Sci.*, vol. 72, No. 3, pp. 928-932.
Aoki et al., (Sep. 1995) "Liposome-mediated in vivo Gene Transfer of Antisense K-ras Construct Inhibits Pancreatic Tumor Dissemination in the Murine Peritoneal Cavity." *Cancer Research*, 55:3810-3816.
Ausuker et al., Editions Short Protocols in Molecular Biology John Wiley & Sons, New. York pp. 72-80, 1989.
Barz et al., (1985) "Characterization of cellular and extracellular plasma membrane vesicles from a non-metastasizing lymphoma (Eb) and its metastasizing variant (EESb)." *Biochimica et Biophysica Acta*, 814:7-84.
Blackburn et al., (1991) "Electrochemiluminescence Detection of Immunoassays and DNA Probe Assays for Clinical Diagnostics." *Clin. Chem.*, vol. 37, No. 9, pp. 1534-1539.

(Continued)

*Primary Examiner*—Suryaprabha Chunduru
(74) *Attorney, Agent, or Firm*—McDonnell Boehnen Hulbert & Berghoff LLP

(57) ABSTRACT

This invention relates to detection of specific extracellular nucleic acid in human or animal blood plasma or serum associated with disease. Specifically, the invention relates to detection of nucleic acid derived from mutant oncogenes or other tumor-associated DNA, and to methods of detecting and monitoring extracellular mutant oncogenes or tumor-associated DNA found in blood plasma or serum. In particular, the invention relates to the detection, identification, or monitoring of the existence, progression or clinical status of neoplasia in humans or other animals that contain a mutation that is associated with the neoplasm through detection of the mutated nucleic acid of the neoplasm in plasma or serum fractions.

33 Claims, No Drawings

OTHER PUBLICATIONS

Bobo et al., (Sep. 1990) "Diagnosis of *Chylamydia trachomatis* Cervical Infection by Detection of Amplified DNA with and Enzyme Immunoassay." *Journal of Clinical Microbiology*, vol. 28, No. 9, 1968-973.

Boland, Richard, (Sep. 1996) "Setting microsatellites free" *Nature Medicine*, vol. 2, No. 9, pp. 972-974.

Boom et al., (Mar. 1990) "Rapid and Simple Method for Purification of Nucleic Acids." *Journal of Clinical Microbiology*, vol. 28, No. 3, pp. 495-303.

Boom et al., (Sep. 1991) "Rapid Purification of Hepatitis B Virus DNA from Serum." *Journal of Clinical Microbiology*, vol. 29, No. 9, pp. 1804-1811.

Bos et al., (May 1987) "Prevalence of ras gene mutations in human colorectal cancers." *Nature*, vol. 327, pp. 293-297.

Carr et al., (Nov. 1985) "Circulating Membrane Vesicles In Leukemic Blood." *Cancer Research*, 45: 5944-5951.

Chaubert et al., (1994) "K-ras Mutations and p53 Alterations in Neoplastic and Nonneoplastic Lesions Associated with Longstanding Ulcerative Colitis." *Amer. Jrnl. Of Path.*, vol. 144, No. 4, pp. 767-774.

Chen et al., (1991) "A Method to Detect ras Point Mutations in Small Subpopulations of Cells." *Analytical Biochemistry*, 195: 51-56.

Chen et al., (Sep. 1996) "Microsatellite alterations in plasma DNA of small cell lung cancer patients." *Nature Medicine*, vol. 2, No. 9, pp. 1033-1035.

Chen et al., "Detecting Tumor-related Alteractions in Plasma or Serum DNA of patients Diagnosed with Breast Cancer," Clinical Cancer Research, Sep. 1999 vol. 5, 2297-2302.

Cheung et al., (Oct. 1994) "Rapid and Sensitive Method for Detection of Hepatitis C Virus RNA by Using Silica Particles." vol. 32, No. 10, pp. 2593-2597.

Chomczynski, Piotr, (1993) "A Reagent For the Single-Step Simultaneous Isolation of RNA, DNA and Proteins from Cell and Tissue Samples." *Biotechniques*, vol. 15, No. 3, pp. 532-536.

Christa et al ., (1992) "Nested polymerase chain reaction of cellular DNA in plasma: a rapid method to investigate th collagen type I A2 MspI polymorphic restriction site in alcoholic patients." *Human Genetics*, 88: 537-540.

Chua et al., 1996, Int. J. Cancer, 69: 54-59.

Cleary et al., "Cloning and Structural Analysis of cDNAs for bcl-2 and a Hybrid bcl-2/Immunoglobulin Transcript Resulting from the t(14;18) Translocation ," Cell. 47:19-28, Oct. 10, 1985.

Coutlee et al., (1989) "Immunodetection of DNA with Biotinylated RNA Probes: A Study of Reactivity of a Monoclonal Antibody to DNA-RNA Hybrids." *Analytical Biochemistry*, 181: 96-105.

DiCesare et al., (1993) "A High-Sensitivity Electrochemiluminescence-Based Detection System for Automated PCR Product Quantitation." *BioTechniques*, vol. 15, No. 1, pp. 152-157.

Emanuel et al., (1993) "Amplification of Specific Gene Products from Human Serum." *GATA*, vol. 10, No. 6, pp. 144-146.

Fearon et al., (Jun. 1990) "A Genetic Model for Colorectal Tumorigenesis." *Cell*, vol. 61, pp. 759-767.

Fearon et al., (Oct. 1987) "Clonal Analysis of Human Colorectal Tumors." *Science*, vol. 238, pp. 193-196.

Fedorov et al., (1987) DNA Assay In Human Blood Plasma. Translated from *Byuleten Eksperimentsl Biologii i Meditsiny*, vol. 102, No. 9, pp. 281-281.

Fey et al., (1991) "The Polymerase Chain Reaction: A New Tool for the Detection of minimal Residual Disease In Haematological Malignancies." *Eur. J. Cancer.*, vol. 27, No. 1, pp. 89-94.

Finney et al., (Jun. 1993) "Predisposition of Neoplastic Transformation Caused by Gene Replacement of H-ras1." *Science*, vol. 260, pp. 1524-1527.

Fournie et al., (1986) "Recovery of Nanogram Quantities of DNA from Plasma and Quantitative Measurement Using Labeling by Nick Translation." *Analytical Biochemistry*, 158: 220/256.

Fournie et al., (Feb. 1995) "Plasma DNA as a marker of cancerous cell death. Investigation in patients suffering from lung cancer and in nude mice bearing human tumours." *Cancer Letters*, 91: 221-227.

Fowke et al., (1995) "Genetic analysis of human DNA recovered from minute amounts of serum of plasma." *Journal of Immunological Methods*, 180, pp. 45-51.

Gocke et al., "p53 and APC Mutations are Detectable in the Plasma and Serum of Patients with Colorectal Cancer (CRC) or Adenomas," Annals New York Academy of Sciences, p. 44-50, vol. 906, Apr. 2000.

Gocke et al., "Serum BCL2/IGH DNA in Follicular Lymphoma Patients: A Minimal Residual Disease Marker," Leukemia and Lymphoma 2000, 39 (1-2) pp. 165-172.

Greenblatt et al., (1994) "Mutations in the p53 Tumor Suppressor Gene: Clues to Cancer Etiology and Molecular Pathogenesis." *Cancer Research*, 54:4855-4878.

Hamilton, Stanley., (Sep. 1992) "Molecular Genetics of Colorectal Carcinoma." *Cancer Supplement*, vol. 70, No. 5, pp. 1216-1221.

Hollstein et al., (1994) "Database of p53 gene somatic mutations in human tumors and cell lines." *Nucleic Acids Research*, vol. 22, No. 17, pp. 3551-3555.

Juckett et al., (Sep. 1982) "Actions of cis-Diamminedichloroplatinum on Cell Surface Nucleic Acids in Cancer Cells as Determined by Cell Electrophoresis Techniques." *Cancer Research*, 42: 3565-3573.

Kahn et al., (1991) "Rapid and sensitive nonradioactive detection of mutant K-ras genes via 'enriched' PCR amplification." *Oncogene*, 6: 1079-1083.

Kamm et al., (1972) "Nucleic Acid Concentrations in Normal Human Plasma." *Clinical Chemistry*, vol. 18, No. 6, pp. 519-522.

Karet et al., (1994) "Quantification of mRNA in Human Tissue Using Fluorescent Nested Reverse-Transcriptase Polymerase Chain Reaction." *Analytical Biochemistry*, 220: 384-390.

Kievits et al., (1991) "NASBA isothermal enzymatic in vitro nucleic acid amplification optimized for the diagnosis of HIV-1 infection." *Journal of Virological Methods*, 35: 273-286.

Kimura et al., 1991, J. Infect Dis. 164:289-293.

Kopreski et al., Somatic Mutation Screening: Identification of Individuals Harboring K-ras Mutations with the Use of Plasma DNA, Journal of the National Cancer Institute, vol. 92, No. 11, Jun. 7, 2000.

Kondo et al., (Mar. 1994) "Detection of Point Mutations in the K-ras Oncogene at Codon 12 in Pure Pancreatic Juice for Diagnosis of Pancreatic Carcinoma." *Cancer*, vol. 23, No. 6, pp. 1589-1594.

Landergren Trends or Genetics 9:199-204, Jun. 1993.

Landgraf et al., (1991) "Direcct Analysis of Polymerase Chain Reaction Products Using Enzyme-linked Immunosorbent Assay Techniques." *Analytical Biochemsitry*, 198:86-91.

Landgraf et al., (1991) "Quantitative Analysis of Polymerase Chain Reaction (PCR) Products Using Primers Labeled with Biotin and a Fluorescent Dye." *Analytical Biochemistry*, 193: 231-235.

Lefort et al., "Point mutations of the K-Ras gene present in the DNA of colorectal tumors are found in the blood plasma DNA of the patients," Proceedings of the American Association for Cancer Research Annual. 36:557, 1995.

Leon et al., (1981) "A Comparison of DNA and DNA-Binding Protein Levels in Malignant Disease." *Europ. J. Cancer*, vol. 17, No. 5, pp. 533-538.

Leon et al., (Mar. 1977) "Free DNA in the Serum of Cancer Patients and the Effect of Therapy." *Cancer Research*. 37: 646-650.

Lowy et al., (Nov. 1991) "Regulation of p21ras Activity." *Trends of Genetics*, 7: 346-351.

Martin et al., (1992) "A Method for Using Serum of Plasma as a Source of DNA or HLA Typing." *Human Immunology*, 33: 108-113.

Mayall et al., J. Clin. Pathol. 1998, 51:611-613.

Mulcahy et al., (Sep. 1996) "Cancer and mutant DNA in blood plasma." *Science*,vol. 348, pp. 628.

Mulcany et al., "A Prospective Study of K-ras Mutations in the Plasma of Pancreatic Cancer Patients," Clinical Cancer Research, 4:271-5 (Feb. 1998).

Nawroz et al., (Sep. 1996) "Microsatellite alterations in serum DNA of head and neck cancer patients." *Nature Medicine*, vol. 2, No. 9, pp. 1035-1037.

Nelson et al., (Feb. 1996) "Detection of K-ras gene mutations in non-neoplastic lung tissue and lung cancers,"*Cancer Letters* 103 (1996) 115-121.

Olsen et a., 1996, Int. J. Cancer 68:415-419.

Oudejans et al., (1991) "Differential Activation of RAS Genes By Point Mutation In Human Colon Cancer With Metastases To Either Lung of Liver." *Int. J. Cancer*, 49: 875-879.

Pellegata et al., (1992) "Detection of K-ras Mutations by Denaturing Gradient Gel Electrophoresis (DGGE): A Study of Pancreatic Cancer." *Anticancer Research*, 12:1731-1736.

Pourzand et al. Mutation Research 288:113-121, Jul. 1993.

Rex et al., Gastroenterology 1997; 11:24-28.

Rhodes et al., (1995) "PCR-Detection of Tumor-Derived p53 DNA in Cerebrospinal Fluid."*Am. J. Clin. Path.*, 103:404-408.

Shapiro et al., (Jun. 1983) "Determination of Circulating DNA Levels in Patients with Benign or Malignant Gastrointestinal Disease." *Cancer*, vol. 51, No. 11, pp. 2116-2120.

Shirasawa et al., (Apr. 1993) "Altered Growth of Human Colon Cancer Cell Lines Disrupted at Activated Ki-ras." *Science*, vol. 260, pp. 85-88.

Sidransky, et al., (1992) "Identification of ras Oncogene Mutations in the Stool of Patients with Curable Colorectal Tumors." *Science*, vol. 256, pp. 102-105.

Sidransky et al., "What we know and what we need to learn," Annals new York Academy of Sciences, pp. 1-4, Apr. 2000.

Sorenson et al., (Jan. 1994) "Soluble Normal and Mutated DNA Sequence from Single-Copy Genes in Human Blood." *Cancer Epidemiology, Biomarkers & Prevention*, vol. 3, pp. 67-71.

Sorenson et al., Detection of Mutated KRAS2 Sequences as Tumor Markers in Plasma/Serum of Patients with Gastrointestinal Cancer, Clinical Cancer Research, 6:2129-37 (Jun. 2000).

Stork et al., (1991) "Detection of K-ras mutations in pancreatic and hepatic neoplasms by non-isotopic mismatched polymerase chain reaction." *Oncogene*, 6: 857-862.

Stroun et al., (1986) "Isolation and Characterization of DNA from the Plasma of Cancer Patients." *European Journal of Cancer*, vol. 23, No. 6, pp. 707-712.

Stroun et al., (1989) "Neoplastic Characteristics of the DNA Found in the Plasma of Cancer Patients." *Oncology*, 46: 318-322.

Tada et al., (Jun. 1993) "Detection of ras Gene Mutations in Pancreatic Juice and Peripheral Blood of Patients with Pancreatic Adenocarcinoma." *Cancer Research*, 53:2472-2474.

Taylor et al., "Shedding of Plasma Membrane Fragements. Neoplastic and Developmental Importance." *Membrane Fragment Shedding*, Chapter 3, pp. 33-57, 1986.

Tseng et al., 1999, J. Clin. Oncol. 17:1391-1396.

Urdea et al., (1991) "Branched DNA amplification multimers for the sensitive, direct detection of human hepatitis viruses."*Nucleic Acids Research*, Symposium Series No. 24, pp. 197-200.

Urdea et al., (1993) Direct and quantitiative detection of HIV-1 RNA in human plasma with a branched DNA signal amplification assay. *Aids*, 7 (suppl. 2): S11-S14.

Vandamme et al., (1995) "Detection of HIV-I RNA in plasma and serum samples using the NASBA amplification system compared to RNA-PCR." *Journal of Virological Methods*, 52:121-132.

Van Mansfeld et al., "PCR-based Approaches for Detection of Mutated ras Genes," PCR Methods and Applications, pp. 211-216, May 1992.

Vasioukhin et al., (1994) "Point mutations of the N-ras gene in the blood plasma DNA of patients with myelodysplastic syndrome of acute myelogenous leukaemia." *British Journal of Haematology*, 86: 774-779.

Vogelstein et al., (Sep. 1988) "Genetic Alterations During Colorectal-Tumor Development." *The New England Journal of Medicine*, vol. 319, No. 9, pp. 525-532.

Wang et al., (Dec. 1989) "Quantitiation of mRNA by the polymerase chain reaction."*Proc. Natl. Acad. Sci.*, vol. 86, pp. 9717-9721.

Winawer et al., The New-Eng. Journal of Medicine vol. 328, No. 13:901-906; Apr. 1, 1993.

Yamagata et al., (Feb. 1994) "Lower Incidence of K-ras Codon 12 Mutation in Flat Colorectal Adenomas than in Polypoid Adenomas." *Jpn. J. Cancer Res.*, 85: 147-151.

\* cited by examiner

DETECTION OF EXTRACELLULAR TUMOR-ASSOCIATED NUCLEIC ACID IN BLOOD PLASMA OR SERUM USING NUCLEIC ACID AMPLIFICATION ASSAY

This application is a divisional of U.S. Ser. No. 10/298,816, filed Nov. 18, 2002, now U.S. Pat. No. 6,939,675, issued on Jul. 31, 2003, which is a continuation of U.S. Ser. No. 09/642,952, filed Aug. 21, 2000, now U.S. Pat. No. 6,521,409, which is a continuation of U.S. Ser. No. 08/818,058, filed Mar. 14, 1997, now U.S. Pat. No. 6,156,504, which is a continuation-in-part of U.S. Provisional Application, Ser. No. 60/028,180, filed Oct. 15, 1996, and U.S. Provisional Application, Ser. No. 60/026,252, filed Sep. 17, 1996, and U.S. Provisional Application, Ser. No. 60/013,497, filed Mar. 15, 1996, each of which provisional applications is now abandoned, the entire disclosure of each of which is hereby incorporated by reference.

BACKGROUND OF THE INVENTION

1. Field of the Invention

This invention relates to methods for detecting specific extracellular nucleic acid in plasma or serum fractions of human or animal blood associated with neoplastic, pre-malignant or proliferative disease. The invention permits the detection of extracellular, tumor-associated nucleic acid in the serum or plasma of humans or other animals recognized as having a neoplastic, pre-malignant or proliferative disease or in individuals without any prior history or diagnosis of neoplastic, pre-malignant or proliferative disease. Specifically, the invention relates to detection of nucleic acid derived from mutant oncogenes or other tumor-associated DNA, and to methods of detecting and monitoring extracellular mutant oncogenes or tumor-associated DNA found in the plasma or serum fraction of blood using DNA enrichment methods, wherein enrichment-based extraction methods are used prior to amplification and/or detection, or wherein enrichment for the nucleic acid of interest occurs during amplification, in particular through use of a restriction endonuclease. In particular, the invention relates to the detection, identification, or inference of the existence of premalignant neoplasms or tissue in humans or other animals without cancer, wherein the neoplasm contains a mutation that is associated with the neoplasm, through detection of the mutated nucleic acid associated with the neoplasm in plasma or serum fractions. The invention provides the ability to detect extracellular nucleic acid derived from genetic sequences known to be associated with neoplasia, such as oncogenes, as well as genetic sequences previously unrecognized as being associated with neoplastic, pre-malignant or proliferative disease. The invention thereby provides methods for early identification of colorectal, pancreatic, lung, breast, bladder, ovarian, lymphoma and other malignancies carrying tumor-related mutations of DNA and methods for monitoring cancer and other neoplastic disorders in humans and other animals.

2. Description of the Related Art

Neoplastic disease, including most particularly that collection of diseases known as cancer, is a significant part of morbidity and mortality in adults in the developed world, being surpassed only by cardiovascular disease as the primary cause of adult death. Although improvements in cancer treatment have increased survival times from diagnosis to death, success rates of cancer treatment are more closely related to early detection of neoplastic disease that enable aggressive treatment regimes to be instituted before either primary tumor expansion or metastatic growth can ensue. A particularly favorable prognosis is achieved if premalignant tissue can be eradicated prior to progression to cancer.

Oncogenes are normal components of every human and animal cell, responsible for the production of a great number and variety of proteins that control cell proliferation, growth regulation, and cell death. Although well over one hundred oncogenes have been described to date with nearly all identified at the deoxyribonucleic acid (DNA) sequence level. It is likely that a large number of oncogenes remain to be discovered.

Mutations in DNA occur as the result of inborn (inherited) genetic errors or acquired (somatic) mutations, often as a result of environmental insults, and have long been recognized as playing a causative role in the development of neoplastic disease. Within the last twenty years the sites of such mutations have been recognized to be within oncogenes, including tumor suppressor genes, and similar tumor-related gene regions including those with DNA microsatellite alterations and hypermethylated genes. Mutation of these genes have been found to be an intrinsic and crucial component of premalignant and malignant growth in both animals and humans. Many malignant tumors or cell lines derived from them have been shown to contain one or more mutated oncogenes, and it is possible that every tumor contains at least one mutant oncogene.

Mutated oncogenes are therefore markers of malignant or premalignant conditions. It is also known that other, non-oncogenic portions of the genome may be altered in the neoplastic state. Nucleic acid based assays can detect both oncogenic and non-oncogenic DNA, whether mutated or non-mutated.

In particular, nucleic acid amplification methods (for example, the polymerase chain reaction) allow the detection of small numbers of mutant molecules among a background of normal ones. While alternate means of detecting small numbers of tumor cells (such as flow cytometry) have generally been limited to hematological malignancies (Dressler and Bartow, 1989, *Semin. Diag. Pathol.* 6: 55-82), nucleic acid amplification assays have proven both sensitive and specific in identifying malignant cells and for predicting prognosis following chemotherapy (Fey et al., 1991, *Eur. J. Cancer* 27: 89-94).

Various nucleic acid amplification strategies for detecting small numbers of mutant molecules in solid tumor tissue have been developed, particularly for the ras oncogene (Chen and Viola, 1991, *Anal. Biochem.* 195: 51-56; Kahn et al., 1991, *Oncogene* 6: 1079-1083; Pellegata et al., 1992, *Anticancer Res.* 12: 1731-1736; Stork et al., 1991, *Oncogene* 6: 857-862). For example, one sensitive and specific method identifies mutant ras oncogene DNA on the basis of failure to cleave a restriction site at the crucial 12th codon (Kahn et al., 1991, ibid.). Similar protocols can be applied to detect any mutated region of DNA in a neoplasm, allowing detection of other oncogene DNA or tumor-associated DNA. Since mutated DNA can be detected not only in the primary cancer but in both precursor lesions and metastatic sites (Dix et al., 1995, *Diagn. Molec. Pathol.* 4: 261-265; Oudejans et al., 1991, *Int. J. Cancer* 49: 875-879), nucleic acid amplification assays provide a means of detecting and monitoring cancer both early and late in the course of disease.

While direct analysis of neoplastic tissue is frequently difficult or impossible (such as in instances of occult, unrecognized disease), peripheral blood is easily accessible and amenable to nucleic acid-based assays such as those mentioned above. Many studies have used nucleic acid amplification assays to analyze the peripheral blood of patients with cancer in order to detect intracellular DNA extracted from circulating cancer cells in patients, including one study which detected the intracellular ras oncogene from circulating pancreatic cancer cells (Tada et al., 1993, *Cancer Res.* 53: 2472-4). However, it must be emphasized that these studies attempt to use nucleic acid-based amplification assays to detect extracted intracellular DNA within circulating cancer cells. The assay is performed on the cellular fraction of the blood from patients having cancer using the cell pellet or cells within whole blood, and the serum or plasma fraction is conventionally ignored or discarded prior to analysis. Since such an approach requires the presence of metastatic circulating cancer cells (for non-hematologic tumors), it is of limited clinical use in patients with early cancers, and it is not useful in the detection of non-hematologic non-invasive neoplasms or pre-malignant states.

It was known in the prior art that small but significant amounts of normal DNA circulate in the blood of healthy people (Fedorov et al., 1986, *Bull. Exp. Biol. Med.* 102: 1190-2; Leon et al., 1977, *Cancer Res.* 37: 646-50), and this amount has been found to increase in cancer states (Shapiro et al., 1983, *Cancer* 51: 2116-20; Stroun et al., 1989, *Oncology* 46: 318-322). The prior art contains disclosure that mutant oncogene DNA could be detected in peripheral blood plasma or serum of cancer patients (see, for example, Sorenson et al., 1994, *Cancer Epidemiology, Biomarkers & Prevention* 3: 67-71; Vasioukhin et al., 1994, *Br. J. Haematol.* 86: 774-9; Vasyukhin et al., in Verna & Shamoo (eds), *Biotechnology Today*, Ares-Serono Symposia Publications, pp. 141-150). Mutant ras oncogenes have been demonstrated in plasma or serum using polymerase chain reaction. However, these reports have also been generally limited to patients with advanced cancer or known neoplastic or proliferative disease.

We have recognized that nucleic acid amplification assays can detect tumor-associated extracellular mutated DNA, including oncogene DNA, in the plasma or serum fraction of blood of humans without clinically-diagnosed cancer or known disease (see U.S. Ser. No. 08/818,058, incorporated by reference), and that this can be accomplished in a clinically useful manner.

SUMMARY OF THE INVENTION

The present invention relates to detection of specific extracellular nucleic acid in plasma or serum in human or animals without cancer which are associated with neoplastic, preneoplastic or proliferative disease or conditions. Specifically, the invention relates to the detection of premalignant disease by the direct enrichment of mutated nucleic acid or tumor-associated nucleic acid found in the plasma or serum fraction of blood with respect to wild-type or non-mutated nucleic acid either prior to or during amplification and detection of the nucleic acid, whereby the concentration of the mutant nucleic acid is increased or the mutant nucleic acid is isolated from the remaining non-mutated nucleic acid. The invention thus provides methods for detecting predictive risk markers for a variety of cancers, including colorectal, pancreatic, lung, prostate, esophageal, gastric, breast, bladder, ovarian, cervical, liver, and kidney cancer, and other malignancies and premalignant conditions carrying tumor-associated mutations in DNA, as well as methods for monitoring neoplastic disorders in humans and animals. The invention provides methods for detecting mutant oncogenes, including but not limited to mutated K-ras, APC, and P53 DNA in plasma or serum. Premalignant diseases or conditions include but are not limited to colorectal adenoma, cervical dysplasia, atypical squamous metaplasia of the lung, bronchial dysplasia, atypical hyperplasia of the breast, prostatic intraepithelial neoplasia, atypical endometrial hyperplasia, dysplastic nevi of the skin, and Barrett's esophagus.

The prior art provides instruction in identifying tumor-associated DNA in the plasma or serum fraction of blood of humans with known malignancy using DNA extraction methods, followed by amplification of the target DNA, followed by detection of the amplified target nucleic acid (see, for example, Sorenson et al., 1993, American Association for Cancer Research Abstract #174; Vasyukhin et al., 1994, *Biotechnology Today* (Verna & Shamoo, eds.), Ares-Serono Symposia Publications, pp. 141-150; Vasioukhin et al., 1994, *Br. J. Haematol.* 86: 774-9; Lefort et al., 1995, American Association for Cancer Research Abstract #557; Nawroz et al., 1996, *Nature Med.* 2:1035-7; Chen et al., 1996, *Nature Med.* 2: 1033-5). However, the prior art does not apply these methods to non-hematologic premalignancy, or to patients without known disease. The methods disclosed herein, in contrast, allow detection of mutant DNA or tumor-associated DNA from the blood of humans without cancer or known disease by providing for the enrichment of mutated nucleic acid, wherein the mutated nucleic acid is concentrated and/or isolated from the remaining extracted nucleic acid prior to or independent of amplification of the target nucleic acid, and thereby provides methods which enable enhanced detection of the target nucleic acid or a fragment thereofs. The methods disclosed herein further provide for the enrichment of mutated nucleic acid with respect to wild-type nucleic acid during amplification of the target nucleic acid, and thereby provide for methods which enable the enhanced detection of the target nucleic acid or a fragment thereofs.

Extracellular DNA is known to circulate in the serum or plasma fraction of blood (Stroun et al., 1987, *Eur. J. Cancer Clin. Oncol.* 23: 707-12; Stroun et al., 1989, *Oncology* 46: 318-322). The invention disclosed in co-owned and co-pending U.S. Ser. No. 08/818,058 (incorporated by reference) taught methods for identifying mutated extracellular DNA for identification of premalignant lesions. These methods are useful for diagnosis and treatment of people who are at risk to develop malignancy or premalignancy. Appropriate therapy, including but not limited to, increased surveillance, surgical excision, chemotherapy and immunotherapy or chemoprevention therapies, as well as more innovative therapies (such as antisense oligonucleotide therapy directed at a mutated KRAS oncogene or vaccine therapy, for example), may be instituted based on detection of mutant or non-mutated tumor-associated nucleic acid in such patients.

Prior to the instant invention and co-owned and co-pending U.S. Ser. No. 08/818,058 it was not known that extracellular mutant nucleic acid could be detected in the blood of humans without cancer. The present invention and co-owned and co-pending U.S. Ser. No. 08/818,058 teach that detection of extracellular mutant nucleic acid in the blood of humans without cancer can be enhanced by enrichment of the mutated nucleic acid relative to wild-type nucleic acid wherein the mutated nucleic acid is concentrated and/or isolated from the remaining extracted nucleic acid in a manner performed either concurrently or sequentially with the extraction and prior to amplification and/or detection of the target nucleic acid or a fragment thereof. Although extracellular mutant tumor-associated DNA has been detected in patients with advanced malignancies (Sorenson et al., 1993, Id.; Vasioukhin et al., 1994, Id.; Nawroz et al., 1996, Id.), it had been presumed in the prior art that only malignancies, and in particular large malignancies, produced enough extracellular DNA to be identified even with prior amplification of the DNA. Co-owned and co-pending U.S. Ser. No. 08/818,058 (incorporated by reference) taught that mutated oncogenes and other tumor-associated nucleic acid was also detectable in blood serum or plasma of individuals with pre-malignant lesions, diseases, or conditions following amplification of nucleic acid sequences found in blood plasma or serum. In the present invention additional methods are taught which enable enrichment of mutated nucleic acid thereby providing enhanced detection of nucleic acid or a fragment thereof whereby detection is indicative or associated with the presence of premalignant tissue in the human.

The present invention provides methods for detecting the presence of extracellular nucleic acid in blood plasma or serum fractions, said nucleic acid being associated with a neoplastic, pre-malignant or proliferative disease state in an animal or a human without cancer. The invention provides methods for extracting and enriching extracellular nucleic acid associated with a neoplastic, pre-malignant or proliferative disease state in an animal or a human prior to nucleic acid amplification or signal detection. The invention further provides for methods whereby mutated nucleic acid is enriched with respect to wild-type nucleic acid during or prior to an amplification step wherein a restriction endonuclease is used during or prior to the amplification step. These methods of the invention are used for the detecting, monitoring, evaluating, or risk assessment of premalignant conditions, and in particular those conditions including but not limited to colorectal adenoma, cervical dysplasia, atypical squamous metaplasia of the lung, bronchial dysplasia, atypical hyperplasia of the breast, prostatic intraepithelial neoplasia, atypical endometrial hyperplasia, dysplastic nevi of the skin, and Barrett's esophagus.

In a first aspect, the invention provides a method for detecting extracellular tumor-derived or tumor-associated mutated nucleic acid in a plasma or serum fraction of a blood sample from a human or animal without cancer, thereby providing a method for diagnosis, detection, monitoring, evaluation or treatment of a neoplastic or proliferative disease in an animal or a human. The method provided by the invention comprises the steps of: first, purifying extracellular nucleic acid from blood plasma or serum to prepare a preparation of extracted nucleic acid containing a tumor-associated mutated nucleic acid or a fragment thereof; second, enriching for the mutated nucleic acid, either concurrent with or sequentially following the initial extraction step, wherein the mutated nucleic acid or a fragment thereof is concentrated and/or isolated from the remaining extracted nucleic acid; third, amplifying the enriched mutated nucleic acid or a fragment thereof, or amplifying a signal corresponding to the enriched mutated nucleic acid or a fragment thereof; and fourth, detecting the product of the amplified mutated nucleic acid or a fragment thereof, or the amplified signal corresponding to the extracted mutated nucleic acid or a fragment thereof, wherein the mutated nucleic acid or a fragment thereof is associated with neoplastic, pre-malignant or proliferative disease. In preferred embodiments of this aspect of the invention, the mutated nucleic acid is derived from nucleic acid encoding a mutated oncogene or other tumor-associated DNA, such as a DNA microsatellite alteration.

In another aspect, the invention provides a method for detecting extracellular tumor-derived or tumor-associated nucleic acid in a plasma or serum fraction of a blood sample from a human or animal without clinically-diagnosed cancer, thereby providing a method for detection, diagnosis, monitoring, evaluation, or treatment of a neoplastic or proliferative disease or premalignant conditions in an animal or a human. The method provided by the invention comprises the steps of: first, purifying extracellular nucleic acid from plasma or serum to prepare a preparation of extracted nucleic acid containing a tumor-associated mutated nucleic acid or a fragment thereof; second, enriching the mutated nucleic acid relative to wild-type nucleic acid using an endonuclease prior to or during amplification; third, amplifying the enriched mutated nucleic acid or a fragment thereof; and fourth, detecting the amplified fragment of the mutated nucleic acid or a signal corresponding to the amplified fragment of the mutated nucleic acid. In preferred embodiments of this aspect of the invention, the nucleic acid is derived from a nucleic acid encoding an oncogene or other tumor-associated DNA.

Particularly preferred embodiments of the invention comprise detection of nucleic acid sequences derived from or related to mutated p53, K-ras, and APC alleles.

In preferred embodiments of the inventive methods, extracellular nucleic acid is extracted from blood plasma or serum using an extraction method including gelatin extraction; silica, glass bead, or diatom extraction; guanidine- or guanidinium-based extraction; chemical extraction methods; and size-exclusion and anion-exchange chromatographic methods. In particularly preferred embodiments, the target DNA is extracted in an enriching manner, or extracted DNA is further enriched, using probe-specific hybridization wherein said hybridizing probes are immobilized to a substrate, wherein such substrate includes but is not limited to nylon and magnetic beads, from which contaminating species (nucleic acid and otherwise) can be removed using methods (such as washing at defined stringencies of salt concentration and temperature) known in the prior art, or wherein alternatively the target DNA of interest may be otherwise isolated from contaminating species including wild-type DNA, for example by application of a magnetic field or an electric field. In preferred embodiments, the extracted and enriched nucleic acid is amplified or signal amplified, wherein the amplification method may include but is not limited to polymerase chain reaction, ligase chain reaction, boomerang DNA amplification, strand displacement amplification, strand displacement activation, cycling probe amplification, and branched DNA signal amplification. In preferred embodiments, DNA detection is performed using a detection method including gel electrophoresis; immunological detection methods; hybridization using a specific, fluorescent-, radioisotope-, antigenic- or chromogenically-labeled probe; Southern blot analysis; electrochemiluminescence; reverse dot blot detection; and high-performance liquid chromatography.

In a preferred embodiment, the nucleic acid is extracted from blood serum or plasma by heating the serum or plasma, at a temperature from about 90° C. to about 100° C., more preferably from about 95° C. to about 100° C., for a time from about 1 minute to about 20 minutes, more preferably from about 5 minutes to about 15 minutes, and most preferably from about 5 minutes to about 10 minutes. Optionally, the blood plasma or serum can be frozen after boiling to a temperature of from about −20° C. to about 0° C. for at least about 5 minutes, more preferably 15 minutes and most preferably for at least about 30 minutes. The boiled blood plasma or serum is used after cooling or, if frozen, after being thawed to a liquid.

The methods of the invention are provided for detecting tumor-associated extracellular nucleic acid, for example a mutated oncogene, in a human without clinically-diagnosed cancer, whereby detection is indicative of the presence of non-hemopoietic cells or tissue containing tumor-associated nucleic acid within the human, the method comprising the steps of purifying extracellular nucleic acid from a plasma or serum fraction of a blood sample from the human to prepare extracted nucleic acid containing a tumor-associated nucleic acid, for example a mutated oncogene DNA, or a fragment thereof, and concurrently or sequentially; enriching for the tumor-associated nucleic acid or a fragment thereof, wherein the tumor-associated nucleic acid or a fragment thereof is concentrated and/or isolated from the remaining extracted nucleic acid; and amplifying or signal amplifying the tumor-associated nucleic acid or a fragment thereof; and detecting the product of the amplified tumor-associated nucleic acid or a fragment thereof or the amplified signal of the tumor-associated nucleic acid or a fragment thereof. The detected nucleic acid or a fragment thereof is then identified, e.g., as comprising the mutated form of an oncogene associated with a neoplastic, pre-malignant or proliferative disease, wherein detection of the amplified product or the amplified signal or the tumor-associated nucleic acid or a fragment thereof is indicative of the presence of non-hemopoietic cells or tissue having a mutated oncogene or other tumor-associated nucleic acid in the human. In a preferred embodiment, the methods of the invention are used as an aid in the diagnosis in a human of a neoplastic, pre-malignant or proliferative disease. In another preferred embodiment, the method is used to determine a predictive risk factor for a neoplastic disease or disease progression in a human. Additionally, the methods of the invention are preferably used to determine disease prognosis in a human. In other preferred embodiments, the methods of the invention are used to determine the need for additional diagnostic tests, or for treatment.

Particularly preferred methods of the invention enable detection in blood of mutated nucleic acid, wherein the mutation is an acquired (somatic) mutation, as may be optionally shown by demonstrating the absence of the mutation in normal cells from the human having the acquired mutation, such as in normal leukocytes or other normal tissue. The invention thus provides a method for determining an acquired predictive risk factor for a non-hematologic disease in a human without clinically-diagnosed cancer, the method comprising the steps of purifying extracellular nucleic acid from blood or blood plasma or serum from a human without clinically-diagnosed cancer to prepare extracted nucleic acid containing a mutated DNA or a mutated DNA fragment, and concurrently or sequentially enriching for the mutated DNA or a fragment thereof, wherein the mutated DNA or a fragment thereof is concentrated and/or isolated from the remaining extracted nucleic acid, and thereafter amplifying the enriched mutated DNA or a fragment thereof, or alternatively amplifying a signal from the enriched mutated DNA or a fragment thereof, and then detecting the product of the amplified mutated DNA or the product of its amplified fragment, or the amplified signal of the mutated DNA or the amplified signal of a fragment thereof, whereby said detection determines a predictive risk factor for a non-hematologic disease. Further, and optionally, by demonstrating the absence of the mutated DNA in normal cells of the human, such as normal leukocytes or other normal tissue, in which it is therefore demonstrated that the mutation is not an inherited or inborn mutation, the predictive risk factor is shown to be an acquired predictive risk factor. In a preferred embodiment the mutated DNA includes but is not limited to either a mutated oncogene DNA, for example mutated K-ras, P53, or APC, or a DNA microsatellite alteration. In preferred embodiments the non-hematologic disease is either colorectal adenoma, cervical dysplasia, atypical squamous metaplasia of the lung, bronchial dysplasia, atypical hyperplasia of the breast, prostatic intraepithelial neoplasia, atypical endometrial hyperplasia, dysplastic nevi of the skin, or Barrett's esophagus.

Also provided as embodiments of the methods of the invention are methods additionally comprising the steps of determining the nucleic acid sequence of the nucleic acid fragment of extracellular nucleic acid in the extracted nucleic acid fraction that is associated with neoplastic or proliferative disease, wherein the nucleic acid sequence of the nucleic acid fragment comprises a mutated or variant allele of a nucleic acid associated with a neoplastic or proliferative disease.

In addition to the methods noted above, the invention provides methods for isolating extracellular tumor-derived or tumor-associated nucleic acid from a fraction of a blood sample comprising the plasma fraction or the serum fraction of the blood sample. In these embodiments the method comprises the steps of purifying extracellular nucleic acid from plasma or serum to prepare a preparation of extracted nucleic acid using an extraction method; enriching the extracted nucleic acid fraction for the portion of the fraction that is associated with neoplastic, pre-malignant or proliferative disease; and cloning the DNA fragments comprising the enriched nucleic acid fraction that is associated with neoplastic, pre-malignant or proliferative disease. Also provided in this aspect of the invention are recombinant genetic constructs comprising a nucleic acid fragment that is associated with a neoplastic, pre-malignant or proliferative disease or condition that is prepared using the methods of the invention. Ribonucleic acid transcribed from the recombinant genetic constructs of the invention are also provided, as well as protein produced from translation of said RNA, and methods for using the translated proteins and peptides of the invention as epitopes for the production of antibodies and vaccines.

The invention also provides a method for concentrating and/or isolating any extracellular mutated DNA or a fragment thereof present in plasma or serum from a human without clinically-diagnosed cancer for which specific oligonucleotide hybridization primers are available, the method comprising the steps of purifying extracellular nucleic acid from blood of a human without clinically-diagnosed cancer to prepare nucleic acid containing a mutated DNA or a mutated DNA fragment, and concurrently or sequentially hybridizing an oligonucleotide to the mutated DNA or a mutated DNA fragment to produce a hybridized product of mutated DNA or a fragment thereof, and separating the hybridized product of mutated DNA or a fragment thereof from the remaining non-hybridized nucleic acid, thereby concentrating and/or isolating the mutated DNA or a fragment thereof. The invention thus provides a method for enriching for a mutated oncogene allele in plasma or serum, including but not limited to mutated K-ras, P53, or APC, and enriching for a DNA having a microsatellite alteration. In a preferred embodiment, the signal from the specific nucleic acid fragments comprising the enriched nucleic acid fraction is amplified using methods known to those with skill in the art, for example, branched DNA signal amplification, and combinations or variations thereof. In a preferred embodiment, detection of specific DNA fragments is performed using a detection method such as gel electrophoresis, immunological detection methods, nucleic acid hybridization using a specific, fluorescent- or chromogenically-labeled probe, Southern blot analysis, electrochemiluminescence, reverse dot blot detection, or high-performance liquid chromatography.

The invention further provides a method for detecting a mutation in the DNA present in blood or a blood fraction, i.e., plasma or serum, of a human having a disease or premalignant condition in whom the presence of the disease or premalignant condition is unrecognized, wherein the mutation is an acquired mutation of known association with the disease or premalignant condition, and wherein the disease or premalignant condition includes but is not limited to colorectal adenoma, cervical dysplasia, atypical squamous metaplasia of the lung, bronchial dysplasia, atypical hyperplasia of the breast, prostatic intraepithelial neoplasia, atypical endometrial hyperplasia, dysplastic nevi of the skin, or Barrett's esophagus. The method comprises the steps of purifying extracellular nucleic acid from blood or a blood fraction from a human in whom the presence of a disease or premalignant condition is unrecognized to prepare extracted nucleic acid containing a mutated DNA or a fragment thereof wherein the mutation is of known association with the disease or premalignant condition, and amplifying the mutated DNA or a fragment thereof, or alternatively amplifying a signal from the mutated DNA or a fragment thereof, and detecting the product of the amplified mutated DNA or a fragment thereof, or the amplified signal of the mutated DNA or a fragment thereof. In a particularly preferred embodiment, the method enables the evaluation of blood or a blood fraction from a human for the mutated oncogene to assist in the identification of the premalignant disease or premalignant condition.

It is therefore the object of this invention to detect or infer the presence of precancerous cells from non-hematologic premalignancies, within a human or animal body having a recognized neoplastic or proliferative disease or in those not previously diagnosed, by examining the plasma or serum fraction of blood for extracellular mutated oncogene DNA or tumor-derived or associated extracellular DNA, using a nucleic acid detection assay.

Another object of this invention is to enable extraction of extracellular tumor-associated nucleic acid from plasma or serum in an enriching manner, wherein the tumor-associated nucleic acid is concentrated and/or isolated from the remaining extracted nucleic acid.

An advantageous application of this invention is to identify, either quantitatively or qualitatively, acquired mutant oncogenes or acquired tumor-associated DNA in the blood plasma or serum of humans or animals as to classify such patients for their risk of neoplastic disease.

Another advantageous application of this invention is to identify, either quantitatively or qualitatively, mutant oncogenes or tumor-associated DNA in the blood plasma or serum of humans or animals who are receiving therapies, including but not limited to chemopreventive therapy and polypectomy, as a guide to whether adequate therapeutic effect has been achieved or whether additional or more advanced therapy is required, and to assess prognosis in these patients.

Another advantageous application of this invention is to identify, either quantitatively or qualitatively, mutant oncogenes or tumor-associated DNA in the blood plasma or serum of humans or animals as to determine the need for additional diagnostic testing, wherein additional diagnostic testing includes but is not limited to endoscopy, colonoscopy, sigmoidoscopy, bronchoscopy, radiologic imaging, radionucleotide scanning, ultrasonography, PET scanning, or further evaluation of organ or site specific bodily fluids or stool, wherein bodily fluid includes but is not limited to that collected by drainage, aspiration, direct sampling, and lavage.

Another advantageous application of this invention is to identify, either by detection or inference, the presence of premalignant neoplasms, conditions, or diseases, through detection of acquired mutant oncogenes or acquired tumor-associated DNA in the blood of humans or animals in whom the presence of the neoplasm, condition, or disease is unrecognized, wherein the acquired mutant DNA derives from premalignant growths such as dysplasias or adenomas, or from other cells bearing an acquired mutated DNA of known association with a premalignant disease or condition, wherein said diseases and conditions include but are not limited to colorectal adenoma, cervical dysplasia, atypical squamous metaplasia of the lung, bronchial dysplasia, atypical hyperplasia of the breast, prostatic intraepithelial neoplasia, atypical endometrial hyperplasia, dysplastic nevi of the skin, and Barrett's esophagus. In addition, the invention advantageously provides a panel of several oncogene assays that can distinguish malignant from premalignant conditions, or assist in medical monitoring to detect transformation of the growth to an outright malignancy, or to detect regression. Furthermore, the invention advantageously provides a means to define risk of malignancy in a human wherein the risk was previously unrecognized. Thus, the invention provides methods for early identification of neoplasms and premalignant conditions of the colon, rectum, pancreas, lung, breast, bladder, ovary, cervix, endometrium, liver, prostate, and stomach and of other neoplasms or premalignant conditions carrying tumor-related mutations of DNA, and methods for monitoring neoplastic disorders in humans and other animals.

Advantageous application of the invention is provided as example but not limitation to include detection of mutated K-ras allele in blood from a human with adenoma; detection of mutated P53 allele in blood from a human with adenoma; detection of mutated APC allele in blood from a human with a colorectal cancer; detection of mutated K-ras allele in blood from a human with a proliferative disease; and detection of mutated K-ras allele in blood from a human with an in-situ (non-invasive or pre-invasive) carcinoma.

Thus, the invention provides a method of screening both healthy individuals and individuals at risk for cancer and premalignant conditions.

Another advantageous application of this invention is to identify, either quantitatively or qualitatively, one or more of multiple mutant oncogenes or tumor-associated DNAs in the blood plasma or serum of humans or animals without clinically-diagnosed cancer or not known to have cancer by use of a panel of oligonucleotide primers each specific for one of multiple differing oncogene alleles detected by the panel, wherein a particularly preferred application employs a nucleic acid enrichment method, and wherein the oncogene alleles are detected concurrently or sequentially. Additionally, said panel enables the inference of the presence of specific tumor types based upon mutated oncogenes or other tumor-associated mutated nucleic acid detected by the panel. Additionally, said panel enhances identification of humans at risk for neoplastic disease. Additionally, said panel enhances identification of humans having premalignant or malignant tissue. A particularly preferred advantageous application of this invention identifies one or more of either K-ras, P53, and/or APC mutated alleles in blood from a human without clinically-diagnosed cancer by use of a panel of primers specific for at least one or more of either K-ras, P53, or APC mutated alleles, whereby a human at risk for a gastrointestinal neoplastic disease is identified.

The invention thereby provides for methods of detecting an acquired mutated APC allele or a fragment thereof in blood or a blood fraction.

Specific preferred embodiments of the present invention will become evident from the following more detailed description of certain preferred embodiments and the claims.

DETAILED DESCRIPTION OF THE INVENTION

This invention provides methods for detecting or inferring the presence of precancerous cells in a human or animal. The method comprises preparation of nucleic acid from plasma or serum wherein the extraction of nucleic acid may be performed with or without DNA precipitation or other separation of soluble nucleic acid from the plasma or serum, and further performed using a method of enrichment for mutated nucleic acid, wherein a mutated nucleic acid is concentrated and/or isolated, in either case followed by detection of mutated nucleic acid preferentially following amplification of the mutated nucleic acid or its signal. Enrichment of the mutated nucleic acid may occur prior to or during amplication by methods provided, including methods using an endonuclease or by methods involving hybridization of the mutated nucleic acid. Embodiments of the invention which provide for enrichment of mutated DNA from blood or blood fractions offer the beneficial advantage of enhancing detection of the mutated DNA. Direct sequencing of mutant nucleic acid is further made possible so that a broad range of mutated oncogenes including tumor suppressor genes, translocated genes, hypermethylated genes, microsatellite alterations in DNA, and non-coding DNA related to the development of malignancy may be identified. Embodiments of the invention provided that exhibit the absence of DNA precipitation methods from the invention serves several beneficial functions. First, such methods reduce the manipulation required for each sample, thus decreasing time and cost in preparation. Second, such decrease in manipulation reduces the risk of contamination of one specimen with another or with exogenous DNA. Third, lack of precipitation steps decrease losses attendant with specimen handling and extraction, thus reducing the sample volume required and potentially increasing the yield of DNA analyzed in each specimen. Fourth, such methods increase the ease with which the entire analytical process may be automated, further reducing costs and turn-around time. Fifth, by reducing the variability in yield inherent in a precipitation process, such methods enable meaningful quantification of mutant nucleic acid, potentially providing prognostic information related to tumor burden.

The invention further provides a number of methods of identifying mutations without prior knowledge of their location to be employed. This significantly increases the utility of detecting mutated DNA in plasma or serum, since genes such as APC and p53 exhibit point mutations throughout their coding regions (Hollstein et al., 1994, Nucleic Acids Res. 22: 3551-5). This is a significant improvement over the prior art, which requires prior knowledge of the location of a mutation or restriction of a search for mutants to the few most frequently mutated loci ("hot spots"; see Sorenson et al., 1993, Id.; Vasioukhin et al., 1994, Id.; Nawroz et al., 1996, Id.; Sorenson et al., 1994, Cancer Epidemiology, Biomarkers & Prevention 13: 67-71). Thus, a larger variety of malignant and premalignant conditions may be assessed (since different tumor types seem to carry particular mutations not found in other tumor types) and they may be detected for more thoroughly. It is to be noted and understood that the methods of DNA preparation and enrichment described herein are furthermore applicable to the previously described aspects of the invention utilizing amplification as well as methods of detection without amplification.

The invention provides methods for detection of an acquired (somatic) DNA mutation in the blood of a human without clinically-diagnosed cancer, wherein normal cells from the human lack the mutation; thereby the invention provides for a method of determining acquired predictive risk factors for non-hematologic acquired diseases and conditions.

Moreover, the assays and methods of the invention can be performed qualitatively, whereby the amount of the nucleic acid product produced is at least sufficient for efficient detection of the product, or quantitatively, whereby the amount of the nucleic acid product produced is measured with reference to a standard useful in determining the significance of the amount of produced nucleic acid (for example, wherein the amount of nucleic acid product is related to a disease state or risk of developing a disease state).

Specifically, the invention provides methods for detecting nucleic acid in plasma or serum of a human or animal without clinically-diagnosed cancer wherein the nucleic acid is associated with the existence of pre-malignant cells or tissues in the human or animal, thereby providing a sensitive predictive risk factor for neoplastic disease and premalignant conditions, wherein such diseases and conditions include but are not limited to colorectal adenoma, cervical dysplasia, atypical squamous metaplasia of the lung, bronchial dysplasia, atypical hyperplasia of the breast, prostatic intraepithelial neoplasia, atypical endometrial hyperplasia, dysplastic nevi of the skin, and Barrett's esophagus.

The invention further provides methods for identification of humans having unrecognized disease who might therefore benefit from additional diagnostic testing, including but not limited to colonoscopy, sigmoidoscopy, endoscopy, bronchoscopy, radiologic imaging including CT scans, spiral CT scans, MRI, contrast studies, and plain films, ultrasonography, radionucleotide imaging, PET scanning, and evaluation of organ specific bodily fluid, stool, or lavage fluid, wherein bodily fluid includes but is not limited to that collected by drainage, aspiration, direct sampling, and lavage.

A General Overview of the Inventive Methods

In the practice of the invention blood is drawn by standard methods into a collection tube, preferably comprising siliconized glass, either without anticoagulant for preparation of serum or with EDTA, heparin, or similar anticoagulants, most preferably EDTA, for preparation of plasma. Plasma may optionally be subsequently converted to serum by incubation of the anticoagulated plasma with an equal volume of 0.025 molar calcium chloride at 37° C. for a brief period, most preferably for 1-3 minutes, until clotting takes place. The clot may then be pelleted by a brief centrifugation (1-10 seconds) at 1,000×g or greater, and the deproteinized plasma removed to another tube. Preferably, the volume of plasma used is 5 µL mixed with 5 µL of calcium chloride, then diluted to 100 µL with water. Alternatively, the centrifugation may be omitted. The serum or plasma may be utilized directly for identification of mutant DNA. In one preferred embodiment, 10 µL of serum or the prepared plasma is heated to a temperature greater than 90° C., most preferably greater than 94° C., for several minutes, most preferably 10. This heated substrate may then be cooled to below room temperature for a period of several minutes, or may be used directly in subsequent steps of the invention. In either instance an optional step of brief centrifugation at 1,000×g or greater may be performed to pellet any precipitate. Alternatively, heating may take place by placing a volume of sample, preferably 5 µL, in a tube or microtiter well under mineral oil and heating in a microwave for greater than 3 minutes, more preferably 3-10 minutes (as described in Sandford et al., 1997, Biotechniques 23: 890-2). In most preferred embodiments, nucleic acid is extracted from plasma or serum as an initial step of the invention. The extraction step may be performed either prior to or concurrent with the enrichment step.

Gelatin Extraction Method

In a preferred embodiment, DNA is co-precipitated from plasma or serum with gelatin by a method modified from that of Foumie et al. (1986, Anal. Biochem. 158: 250-256). A stock 5% (w/v) gelatin solution is prepared by mixing 1 gram gelatin (G8-500, Fisher, Pittsburgh, Pa.) with 20 mL sterile, double-distilled water, autoclaving for 30 minutes, and filtering through a 0.2 micron filter. The resultant solution is sequentially frozen in a dry ice/ethanol bath and thawed at room temperature for a total of five cycles. A working 0.3% gelatin solution is prepared by heating the stock solution to 60° C. and mixing 600 µL of 5% gelatin with 25 µL of 1 M Tris-HCl (pH 8.0) and 9.4 mL of sterile, double-distilled water.

Plasma or serum (160 µL) is mixed with 12.8 µL of 0.5 M EDTA and 467 µL of sterile, double-distilled water, then emulsified for 3 minutes with 320 µL of phenol or phenol:chloroform:isoamyl alcohol (25:24:1 ratio). The solution is centrifuged at 14,000×g for 10 minutes, and 570 µL of the aqueous layer is removed to a clean tube. DNA is precipitated by addition of 142 µL of the 0.3% gelatin working solution and of 500 µL of cold absolute ethanol, followed by incubation at −20° C. for 1-2 hours. Extracellular DNA may be precipitated within less than 1 h of incubation at −20° C., and a very short incubation may be preferable in some circumstances. Alternatively, longer incubation at −20° C. for 1-2 hours insures the precipitation of most DNA. The sample is centrifuged at 14,000×g at 4-6° C. for 15 minutes, washed once with cold 70% ethanol, and dried in a 60° C. heat block for 10 minutes. DNA is then recovered by the addition of 35 to 70 µL of sterile, double-distilled water preheated to 60° C.

Glass Bead, Silica Particle, or Diatom Extraction Method

As an alternative rapid method of extracting extracellular DNA from plasma or serum, glass beads, silica particles, or diatoms may be used, as in the method or adaptation of Boom et al. (Boom et al., 1991, *J. Clin. Microbiol.* 29: 1804-1811; Boom et al., 1989, *J. Clin. Microbiol.* 28: 495-503). Size fractionated silica particles are prepared by suspending 60 grams of silicon dioxide ($SiO_2$, Sigma Chemical Co., St. Louis, Mo.) in 500 mL of demineralized sterile double-distilled water. The suspension is then settled for 24 hours at room temperature. Four-hundred thirty (430) mL of supernatant is removed by suction and the particles are resuspended in demineralized, sterile double-distilled water added to a final volume of 500 mL. After an additional 5 hours of settlement, 440 mL of the supernatant is removed by suction, and 600 µL of HCl (32% wt/vol) is added to adjust the suspension to a pH 2. The suspension is aliquotted and stored in the dark.

Lysis buffer is prepared by dissolving 120 grams of guanidine thiocyanate (GuSCN, Fluka Chemical, Buchs, Switzerland) into 100 ML of 0.1 M Tris hydrochloride (Tris-HCl) (pH 6.4), and 22 mL of 0.2 M EDTA, adjusted to pH 8.0 with NaOH, and 2.6 grams of Triton X-100 (Packard Instrument Co., Downers Grove, Ill.). The solution is then homogenized.

Washing buffer is prepared by dissolving 120 grams of guanidine thiocyanate (GuSCN) into 100 mL of 0.1 M Tris-HCl (pH 6.4).

50 µL of plasma or serum are mixed with 40 µL of silica suspension prepared as above, and with 900 µL of lysis buffer, prepared as above, using an Eppendorf 5432 mixer over 10 minutes at room temperature. The mixture is then centrifuged at 12,000×g for 1 minute and the supernatant aspirated and discarded. The silica-DNA pellet is then washed twice with 450 µL of washing buffer, prepared as above. The pellet is then washed twice with 1 mL of 70% (vol/vol) ethanol. The pellet is then given a final wash with 1 mL of acetone and dried on a heat block at 56° C. for ten minutes. The sample is eluted for ten minutes at 56° C. with a TE buffer consisting of 10 mM Tris-HCl, 1 mM EDTA (pH 8.0) with or without Proteinase K (100 ng/ml) as described by Boom et al., ibid. Following elution, the sample is then centrifuged at 12,000×g for three minutes, and the DNA-containing supernatant recovered (Boom et al., 1991, ibid.; Boom et al., 1989, ibid.; Cheung et al., 1994, *J. Clin. Microbiol.* 32: 2593-2597).

Acid Guanidinium Thiocyanate-Phenol-Chloroform Extraction Method

As an alternative method, extracellular DNA may be extracted from plasma or serum in one step using variations of the acid guanidinium thiocyanate-phenol-chloroform extraction method. For example, extracellular DNA may be extracted from plasma or serum using TRI reagent, a monophase guanidine-thiocyanate-phenol solution, as described by Chomczynski (1993, *Biotechniques* 15: 532-534). Plasma or serum (1 mL) is processed using 5-10 mL of TRI Reagent (commercially available as TRI Reagent, Molecular Research Center, Cincinnati, Ohio, and from other sources) according to manufacturer's directions. DNA is precipitated from the interphase with ethanol.

Other commercially available kits known to the art may be utilized to extract nucleic acid from plasma or serum providing purified DNA for use in the invention's first step, including Qiagen columns (QIAamp blood kit, Qiagen, Basel, Switzerland), Boehringer Mannheim's High-Pure Viral Nucleic Acid kit, and other commercial kits for extraction of nucleic acid from plasma or serum as described herein, which are provided as example and not as limitation. Such kits may be used according to manufacturer's directions.

Enrichment Methods

Extracellular nucleic acid can be enriched from plasma, serum or whole blood using hybridization methods specific for particular species on extracellular nucleic acid. For example, nucleic acid derived from mutant K-ras oncogene DNA can be enriched from whole blood, serum or plasma using specific oligonucleotides for hybridization. Such oligonucleotides, generally ranging in size from about 12 to about 15 nucleotides or longer, are advantageously centered around the mutated nucleotide of interest to provide the greatest degree of discrimination between mutant and wildtype alleles. In particular, for the K-ras oncogene, the nucleotides of interest are the first and second positions of codons 12, 13 and 61. For K-ras, codon 12, first position, exemplary oligonucleotides have the sequence:

```
GTTGGAGCTCGTGGCGTAG          (SEQ ID No.: 1)

GTTGGAGCTTGTGGCGTAG          (SEQ ID No.: 2)

and

GTTGGAGCTAGTGGCGTAG,         (SEQ ID No.: 3)
``` where the underlined nucleotide in each oligonucleotide is mutated from the wildtype.

In another example, many mutations associated with the development of malignancy have been identified in the tumor suppressor gene p53 from a number of different tumors and tumor types. In colorectal carcinoma, for example, the most common mutation involves codon 175. For this mutation, exemplary enrichment oligonucleotides include the following:

```
CCATGAGCACTGCTCAG            (SEQ ID No.: 4)

CCATGAGCTCTGCTCAG            (SEQ ID No.: 5)

and

CCATGAGCCCTGCTCAG,           (SEQ ID No.: 6)
``` where the underlined nucleotide in each oligonucleotide is mutated from the wildtype.

It will be apparent to one of ordinary skill in the art that any DNA point mutation can be enriched using oligonucleotides specific for the mutation and prepared to encompass the mutated site.

Additionally, enrichment oligonucleotides can be prepared to enrich for a particular gene such as an oncogene regardless of the presence of a mutation by preparing an oligonucleotide specific for the gene that does not encompass a site known to be involved in mutation related to the development of malignancy. Using such enrichment strategies, mutated nucleic acid is subsequently identified in the detection step of the methods of the invention, using mutation-specific oligonucleotides in hybridization assays, for example, or during a selective amplification step. For K-ras, enrichment oligonucleotides for nucleic acids encoding regions other than those containing codons 12, 13 or 61 are used to enrich a plasma, serum or whole blood sample for K-ras encoding nucleic acid sequences, both mutant and wildtype. Differentiation between mutant and wildtype fragment is then accomplished using detection methods such as allele-specific oligonucleotide hybridization assays.

Advantageously, more than one enrichment oligonucleotide species can be used simultaneously or sequentially. A panel of such enrichment oligonucleotides could include oligonucleotides specific for different mutated sites in a particular oncogene, or several mutated oncogenes in a multiplex enrichment assay. Differential detection methods, such as hybridization with distinguishable detectable labels, are then used to detect the different mutated nucleic acids resulting from the enrichment step of the methods of the invention.

Additional enrichment oligonucleotides include those oligonucleotides disclosed in co-owned and co-pending U.S. Ser. No. 08/818,058, the disclosure of which is explicitly incorporated herein.

Additional Nucleic Acid Extraction Methods

Alternate means of purification which may be used to obtain DNA from serum or plasma, including selective retention on a size exclusion column or similar matrix, salting-out method, and other guanidinium thiocyanate extraction methods known in the art, including but not limited to all methods described in co-owned and co-pending U.S. Ser. No. 08/818, 058.

Alternatively, the plasma or serum may be prepared as described above, and one or several regions of DNA of interest may be enriched. This may be performed by hybridization of nucleic acid in the heated plasma or serum solution or of extracted nucleic acid against a manufactured strand of nucleic acid that is complementary to the sequence of interest (an affinity capture approach; see Seeger et al., 1997, *Biotechniques* 23: 512-7). Such "capturing" nucleic acids may consist of oligonucleotides, DNA or RNA constructs, or peptide nucleic acids. The capture of the target DNA serves as a means of enriching the target at the expense of other, non-hybridizing DNA that would otherwise compete with the target DNA during subsequent detection. The enrichment procedure occurs by hybridization at a low temperature under nonstringent conditions (see generally, Sambrook et al., 1989, *Molecular Cloning: A Laboratory Manual*. (2nd ed.) Cold Spring Harbor Laboratory Press, New York), followed by washing of the target-capture complex to remove unbound, competing DNA. The capture nucleic acid may be bound to a surface, such as the wall of a tube or a nylon or other membrane, or it may be bound to glass, magnetic or other beads that are incubated with the serum or plasma (Gelsthorpe et al., 1997, *Biotechniques* 22:1080-2; Rudi et al., 1997, *Biotechniques* 22: 506-11), thereby enabling separation of the mutated nucleic acid alleles from wild-type nucleic acid alleles, for example but not limitation, by using a magnetic or electric field, or by other methods well known to the art. A single region of interest may be examined in each sample, or several regions may be enriched for. By judicious choice of capturing nucleic acids, more than one target DNA may be captured simultaneously. It will be understood by one skilled in the art that this multiplexing approach will speed analysis of samples, and may be performed in a relatively tumor-specific fashion, i.e., with a set of capture probes representing genes that are mutated frequently in one type of tumor and infrequently in others. As an example, the genes TP53, KRAS, DCC and APC are often mutated in colorectal cancers and colorectal adenomas (precancerous tumors), while VHL and WT1 are more often mutated in renal cell carcinomas. Thus, the identification of mutations in a series of genes or tumor-associated DNA may, beyond identifying the presence of a malignancy or premalignancy in a patient, serve to identify the particular type of neoplasia by the particular set of genes or tumor-associated DNAs mutated or predict for the location of the neoplasia. Additionally, methods involving enrichment of the target nucleic acid may be performed on unprocessed plasma, serum or whole blood.

Alternatively, other means of enriching for the nucleic acid of interest in a plasma or serum sample may be used. For example, antibodies directed against any portion of the target DNA may serve to capture it, with subsequent identification of the presence or absence of mutations. However, several antibodies may be needed to capture the entire gene or DNA of interest if this is desired, since we and others have found that DNA in plasma or serum often circulates in relatively small pieces, on the order of several hundred base pairs in length. Such capturing antibodies may be raised in animals by immunization with the target DNA or fragments thereof, or may be purified from naturally occurring anti-DNA antibodies found in humans with rheumatologic conditions. As explained above, the capturing antibodies may be bound to tubes or wells as in an ELISA, or may be bound to tubing through which a sample travels prior to further analysis, as by gas chromatography/mass spectroscopy or high performance liquid chromatography or bound to beads. These means and methods are provided by way of example and are not intended to be limiting.

Following the preparation of plasma or serum as described above, and preferably following an amplification step, a detection step for mutations in oncogenes or tumor-associated DNA is performed. It is the detection of mutants that indicates the presence of one or more mutant-bearing cells within the patient. Moreover, as explained above, the pattern of mutants may be relatively specific for different types of proliferative diseases. It bears stressing that this invention, comprising either precipitation of extracellular DNA from serum or plasma or preparation of serum, plasma or whole blood for analysis without precipitation of DNA followed by detection of mutations (including, but not limited to, point mutation, insertion, deletion and translocation) may be applied to detection of malignant neoplasms and detection of precursor, premalignant conditions.

A mutated DNA detected in blood plasma or serum of a human may be further characterized as being an acquired (somatic) mutation by demonstrating the absence of the mutation in normal cells of the human using methods known in the art consisting of extraction of the DNA from normal cells, and amplifying for the mutated DNA of interest in a manner as to enable detection, wherein an absence of the mutated DNA in normal cells from the human indicates the mutation detected within blood plasma or serum DNA to be an acquired mutation, and not an inherited or inborn mutation.

Detection of DNA sequence mutants may proceed by any of a number of methods known to those skilled in the art (Kilger et al., 1997, *Nucleic Acids Res.* 25: 2032-4). The sequence may be detected directly by nucleic acid sequencing methods such as cycle sequencing (Sarkar et al., 1995, *Nucleic Acids Res.* 23: 1269-70) or direct dideoxynucleotide sequencing, in which some or all of the enriched DNA of interest that has been harvested from plasma or serum is used as a template for sequencing reactions. An oligonucleotide primer or set of primers specific to the gene or DNA of interest is used in standard sequencing reactions.

Other methods of DNA sequencing, such as sequencing by hybridization, sequencing using a "chip" containing many oligonucleotides for hybridization (as, for example, those produced by Affymetrix Corp.; Ramsay et al., 1998, *Nature Biotechnology* 16: 40-44; Marshall et al., 1998, *Nature Biotechnology* 16: 27-31), sequencing by HPLC (DeDionisio et al., 1996, *J Chromatogr A* 735: 191-208), and modifications of DNA sequencing strategies such as multiplex allele-specific diagnostic assay (MASDA; Shuber et al., 1997, *Hum. Molec. Genet.* 6: 337-47), dideoxy fingerprinting (Sarkar et al., 1992, *Genomics* 13: 441-3; Blaszyk et al., 1995, *Biotechniques* 18: 256-60; Martincic et al., 1996, *Oncogene* 13: 2039-44), and fluorogenic probe-based PCR methods (such as Taqman; Perkin-Elmer Corp.; Heid et al., 1996, *Genome Res.* 6: 986-94) and cleavase-based methods may be used. Alternatively, approaches that detect specific mutations of interest such as allele-specific amplification or restriction digest methods such as CARD (as disclosed in co-owned and co-pending U.S. Ser. No. 08/818,058, incorporated by reference) may be used singly or in combination to identify extracellular mutant DNA (Zafiropoulos et al., 1997, *Biotechniques* 23:1104-1109). It will be clear to one skilled in the art that a variety of suitable methods for determining mutations at the DNA sequence level would suffice for the practice of this step of the inventive methods, and the methods mentioned herein are not intended to be comprehensive or limiting, but merely to serve as examples.

Methods that detect mutations in DNA without precisely identifying the mutated base or bases are also able to be used in this invention, inclusive of those methods of detection previously described in the application. Single strand conformation polymorphism (SSCP) analysis, for example, can identify variations from wildtype in a region of DNA without precisely defining the mutated base(s)(Orita et al., 1989, *Proc. Natl. Acad. Sci. USA* 86: 2766-70; Suzuki et al., 1990, *Oncogene* 5:1037-43). Similarly, heteroduplex analysis (Glavac et al., 1995, *Hum. Mutat.* 6(4):281-7), denaturing gradient gel electrophoresis (Pellegata et al., 1992, *Anticancer Res.* 12:1731-1736) and mismatch cleavage assays can identify a patient carrying a DNA mutation by analysis of extracted or unextracted plasma or serum DNA. All of these procedures require cleavage of the sample DNA with restriction endonucleases, or alternatively amplification by PCR or a similar amplification technique, to obtain uniform sized DNA fragments for gel electrophoresis analysis.

Detection of the target mutations can also be accomplished by means of signal amplification techniques. For example, the branched DNA assay (Chiron) uses a specific DNA probe to a target DNA (in this case, any of the oncogenes or tumor-associated DNAs of interest) to identify the presence of the target (Urdea et al., 1993, *AIDS* 7: S11-4). The signal is amplified by means of modifications made to the probe which allow many fluorescent detector DNA molecules to hybridize to a target nucleic acid. Similarly, oligonucleotide ligation assays may be used to amplify and detect the mutation of interest from amplified or directly processed serum or plasma DNA (Benson et al., 1996, *Thromb. Res.* 83: 87-96). Any signal amplification method may be used in the invention.

For the purposes of this invention, tumor-derived or associated DNA includes but is not limited to DNA related to mutated oncogenes or other mutated DNA, a partial list of which includes H-ras, K-ras, N-ras, c-myc, her-2/neu, bcr-abl, fms, src, fos, sis, jun, bcl-2, bcl-2/IgH, or VHL (Von Hippel-Lindau gene), and DNA microsatellite alterations; DNA related to tumor suppressor genes, a partial list of which includes p53, RB, MCC, APC, DCC, NF1, WT1; and hypermethylated DNA.

It will be understood that methods of detection and/or enrichment for extracellular mutated nucleic acid from blood or blood fractions as described herein may similarly be applied as methods for detection and/or enrichment of extracellular mutated nucleic acid present in other bodily fluids, including particularly ascitic fluid, pleural effusions, pericardial effusions, sputum and bronchial secretions, breast fluid including secretion from the ducts and nipple of the breast, gastric secretions, and fluid aspirated or drained from cystic or semi-cystic tissues, wherein evaluation of the bodily fluid offers distinct diagnostic advantage in humans in whom the presence of a disease is unknown.

Methods of Enrichment using an Endonuclease

Enrichment of the target or mutated nucleic acid, whereby the concentration of the target nucleic acid is increased with respect to wild-type or non-mutated nucleic acid, may be accomplished by using an endonuclease either before or during an amplification step, as disclosed in co-owned and co-pending U.S. Ser. No. 08/818,058, the disclosure of which is explicitly incorporated herein. In preferred embodiments, the endonuclease may be BstNI, HinP I, or Msp I.

Therapeutic Applications

The extraction of extracellular DNA from plasma or serum permits further analysis or other manipulation of that DNA, from which further clinical utility is realized. In this optional step of the invention, extracellular nucleic acid is analyzed to define the characteristics or composition of the tumor or pre-neoplastic lesion from which the nucleic acid originates. Any of several methods may be used, dependent upon the desired information, including nucleic acid sequencing, spectroscopy including proton NMR spectroscopy, biochemical analysis, and immunologic analysis. In the preferred embodiment, such nucleic acid is cloned into a plasmid vector, for example the pGEM-T vector plasmid (Promega, Madison, Wis.) and sequenced using a commercial kit such as Sequenase 2.0 (USB, Cleveland, Ohio). Analysis to define the characteristics or composition of the extracellular nucleic acid, and thus the characteristics of the originating tissue, affords a wide array of clinical utility, including the description, characterization, or classification of the tumor, whether known or occult, by tissue of origin, by type (such as premalignant or malignant), phenotype, or genotype, or by description or characterization of tumor behavior, physiology and biochemistry. This information is useful to characterize the lesion for tumor invasiveness, propensity to metastasize, and sensitivity or resistance to various therapies, thereby allowing the prediction of response to either ongoing or planned therapy and, further, allowing evaluation of prognosis. Comparison of the characteristics of extracellular nucleic acid to previous biopsy or surgical specimens permits further evaluation of tumor heterogeneity or similarity in comparison to that specimen, and thus evaluation of tumor recurrence or progression.

Following extraction of extracellular DNA from plasma or serum, complimentary ribonucleic acid (RNA) may be transcribed or manufactured from the DNA. In a preferred embodiment, transcription of RNA is performed by employing a primer with an RNA polymerase promoter region joined to the standard primer sequence for the DNA of interest. RNA complimentary to the DNA is then transcribed from the attached promoter region. In an alternative method, extracellular nucleic acid is cloned into an expression vector, and RNA complimentary to the DNA is transcribed. Furthermore, as an optional preferred embodiment, the complimentary RNA is used in an in vitro translation reaction to manufacture tumor-associated or tumor-specific protein.

Extraction of extracellular nucleic acid from blood serum or plasma, and characterization, transcription of complimentary RNA, and translation to tumor-associated or tumor-specific protein, provides significant utility, both in the delineation of those who might benefit from therapy, including chemoprevention or assignment of therapy, and in the development of tumor-specific therapies. Sequencing of extracellular nucleic acid or transcription of complementary RNA allows identification or development of antisense compounds, including synthetic oligonucleotides and other antisense constructs appropriately specific to the extracellular DNA, such as by construction of an expression plasmid such as by adapting the method of Aoki et al. (1995, Cancer Res. 55: 3810-3816). Similarly, defining tumor characteristics allows identification of specific monoclonal antibody or vaccine therapies appropriately specific to the extracellular DNA. Production of corresponding immunologic protein can be used in the development of tumor-specific monoclonal antibodies. Similarly, translated protein can be used in tumor-specific vaccine development. Furthermore, the extracellular DNA permits a means of defining or allowing the construction of a DNA construct which may be used in vaccine therapy.

Of particular value, the invention allows the development and application of tumor-specific therapies even when only premalignant tumors, early cancers, or occult cancers are present. Thus, the invention allows therapeutic intervention when tumor burden is low, immunologic function is relatively intact, and the patient is not compromised, all increasing the potential for cure.

The invention also provides methods for transcribing RNA complementary to the isolated extracellular nucleic acid from plasma or serum, as well as methods for producing peptides and proteins (or fragments thereof) encoded thereby. Additional methods for using the peptide and proteins as antigens for producing antibodies specific for the peptides and proteins encoded by the extracellular nucleic acids of the invention are also provided. The isolated extracellular nucleic acids of the invention are also used in methods for producing antisense oligonucleotides, either synthetically or using recombinant genetic methods, and the use thereof for affecting gene expression in a cell will be appreciated by one having ordinary skill in the art in view of the methods for isolating and identifying said extracellular nucleic acid provided herein. Vaccine production, as is understood by one with skill in the art, is also enabled using the methods of the invention.

The methods of the invention and preferred uses for the methods of the invention are more fully illustrated in the following Examples. These Examples illustrate certain aspects of the above-described method and advantageous results. These Examples are shown by way of illustration and not by way of limitation.

EXAMPLE 1

Detection of Mutated K-ras DNA in the Plasma of Patients without Clinically-Diagnosed Cancer using an Endonuclease-Based Enrichment Method Colorectal adenomas are common premalignant neoplasms associated with a risk for development of colorectal cancer. Blood plasma was prospectively obtained from 25 individuals who had K-ras mutated colorectal adenoma. None of the individuals were known to have cancer, nor did colonoscopy or other testing demonstrate cancer in any individual. Five to ten milliliters of blood was collected from each individual, and plasma was fractionated from the whole blood by centrifugation at 400×g at room temperature for ten minutes. Extracellular DNA was then extracted from the plasma using a gelatin precipitation method as previously described. The extracted plasma DNA was amplified with a polymerase chain reaction assay which enriched for mutated K-ras by employing simultaneous restriction digestion and PCR amplification utilizing a BstNI restriction endonuclease, the method of which (CARD) is described in full in co-owned and co-pending U.S. Ser. No. 08/818,058, the disclosure of which is explicitly incorporated herein. Mutations in the final digested amplified product were identified by agarose gel electrophoresis, and further prior to final enzyme digestion by identification of altered bases using dot blot hybridization. Following amplification, 5 µL of product were applied to a nylon membrane (MSI, Westboro, Mass.). Replicate blots were hybridized to $^{32}$P-radiolabelled oligonucleotides designed to identify point mutations in positions 1 and 2 of codons 12 of the K-ras gene (Mutaprobe Human K-ras 12 set, Oncogene Science, Uniondale, N.Y.). Hybridization and wash conditions were as specified by the membrane's manufacturer. Blots were exposed to x-ray film for 10 hours at −80° C. Mutated K-ras DNA was detected in the plasma of 20 individuals. Sequence analysis demonstrated that the altered base mutation found in the adenoma was similarly demonstrable in the plasma of the individuals.

This example demonstrates that an enrichment-based assay enables detection of mutated nucleic acid in individuals without clinically-diagnosed cancer; further enables detection of the presence of premalignant tissue including colorectal adenoma; further enables identification of a predictive risk factor; further enables sequence identification of the mutated DNA in blood and further predicts for the sequence of the mutated DNA in tissue.

EXAMPLE 2

Detection of Mutated P53 DNA in the Plasma of Individuals without Clinically-Diagnosed Cancer using an Enrichment Assay P53 mutations are common oncogene mutations in both malignant and premalignant tumors. Plasma was obtained prospectively from individuals undergoing colonoscopy and assayed for plasma DNA containing DNA species of P53 mutations at codons 175 and 248. Five to ten milliliters of blood were collected in EDTA-coated siliconized glass vacutainer tubes from each individual assayed. Plasma was fractionated from whole blood by centrifugation at 400×g at room temperature for ten minutes. Extracellular DNA was then extracted from plasma using a gelatin precipitation extraction as previously described. 7 µL of the gelatin-precipitated DNA were then used in an amplification reaction in which P53 DNA was enriched using a restriction endonuclease. Oligonucleotide primers were designed to perform a hemi-nested amplification of a portion of exon 5 for codon 175, wherein the first primer (P53-1) is 5'-GCAGTCACAGCACAT-GACG-3' (SEQ ID No. 7); the second primer (P53-2) is 5'-AATCAGAGGCCTGGGGAC-3' (SEQ ID No. 8); and the third primer (P53-3) is 5'-GGGCCAGACCTAAGAGCAAT-3' (SEQ ID No. 9). A reaction mixture consisting of 1×Taq polymerase (Fisher, Pittsburgh, Pa.) in a volume of 50 μL was prepared. This mixture was amplified by polymerase chain reaction under mineral oil for 20 cycles with denaturation at 94° C. for 1 minute, annealing at 58° C. for 90 seconds, and extension at 72° C. for 90 seconds. This was followed by a CARD step of combined amplification and restriction digestion, in which 5 μL of the initial amplification product was transferred to a new reaction mix identical to the K-ras mixture previously described for CARD in co-pending and co-owned U.S. Ser. No. 08/818,058, the disclosure of which is explicitly incorporated herein, except for the use of 10 picomoles each of primers P53-1 and P53-2 in place of K-ras primers, and the substitution of 8 units of restriction enzyme HinP1 I (New England BioLabs, Beverly, Mass.) for BstNI. Cycling parameters were as for the CARD K-ras amplification. A final digestion with HinP1 I was performed prior to identification of mutants by agarose gel electrophoresis. To detect codon 248 P53 mutations a similar CARD assay was performed using primers (P53-4): 5'-TTGGGCCGGTGT-TATCTC-3' (SEQ ID No. 10); and (P53-5): 5'-ATGGTGCG-GATGGGCCTC-3' (SEQ ID No. 11), designed to amplify a portion of exon 7. Mutations at codon 248 were enriched and amplified in the same manner as described above for codon 175, except substituting HinP1 I with Msp I (New England BioLabs, Beverly, Mass.). Mutations in the final digested amplified product were identified by agarose gel electrophoresis.

Extracellular mutated P53 DNA was demonstrated in the plasma of 3 individuals, none of whom had clinically-diagnosed cancer, including one individual having a codon 175 P53 mutation, and 2 individuals having a codon 248 P53 mutation. Colonoscopy demonstrated a premalignant lesion (an adenoma) in each of two of these individuals, and a proliferative disease (a hyperplastic polyp) in the third individual.

This example further demonstrates that extracellular mutated nucleic acid can be detected in the blood of humans without clinically-diagnosed cancer; further that enrichment of the target nucleic acid may be accomplished using a restriction endonuclease; further that mutated P53 DNA may be detected in the blood of humans without clinically-diagnosed cancer; further that mutated P53 DNA may be enriched from the blood of humans without clinically-diagnosed cancer; further that mutated P53 DNA may be detected in the blood of individuals with premalignant neoplasms or proliferative disease; further that P53 DNA provides a predictive risk factor for neoplastic disease. While the example demonstrates detection of P53 mutations at codon 175 and 248, P53 mutations at other codons may similarly be detected in blood by substituting the appropriate primers and restriction enzyme.

EXAMPLE 3

Enhanced Identification of Humans with Premalignant Neoplasms using a Multiplex Assay or Assay Panel Targeting Differing Mutated Oncogenes Since individuals with premalignant neoplasms and conditions may harbor differing mutated oncogenes or differing DNA microsatellite alterations, evaluating blood for a number of differing mutated oncogenes or tumor-associated nucleic acids are thereby more likely to enable identification of those individuals harboring neoplasms, thereby increasing overall sensitivity in identification of said individuals.

Plasma was evaluated by a panel of assays which detect mutated K-ras DNA (by the method provided in example 1), and mutated P53 DNA (by the method provided in example 2). Plasma from individuals without clinically-diagnosed cancer shown to harbor colorectal adenoma were evaluated for both extracellular mutated K-ras and mutated P53 DNA. Mutated K-ras but not P53 DNA was demonstrated in the plasma from 20 individuals having K-ras mutated adenoma. However, mutated P53 but not K-ras DNA was additionally demonstrated in the plasma from 2 individuals having wild-type ras adenoma. Together, the panel of both K-ras and P53 assays thereby enabled increased identification of individuals with colorectal adenoma. Increasing the number of mutated oncogenes and tumor-associated nucleic acids detected by the assay array or panel (for example but not limitation by including an APC assay as provided in example 4) thereby increases the ability to identify individuals harboring premalignant neoplasms, thereby increasing the utility of the assay.

EXAMPLE 4

Detection of an APC Gene Mutation in Plasma from an Individual with a Colorectal Neoplasm APC gene mutations are common mutations in colorectal premalignant and malignant neoplasms. APC mutations may be demonstrated in blood or tissue by the method as follows: Three overlapping sets of oligonucleotide primers are prepared to the mutation cluster region in exon 15 of the APC gene, which are estimated to account for over 60% of all APC mutations in colorectal neoplasms. The primer sequences are:

APC-1, 5'-TCCACACCTTCATCTAATGCC-3'; (SEQ ID No. 12)

APC-2, 5'-CATTCCACTGCATGGTTCAC-3'; (SEQ ID NO. 13)

APC-3, 5'-CTGAAGATCCTGTGAGCGAA-3'; (SEQ ID No. 14)

APC-4, 5'-TCAGGCTGGATGAACAAGAA-3'; (SEQ ID No. 15)

APC-5, 5'-CTTCGCTCACAGGATCTTCA-3'; (SEQ ID No. 16)

APC-6, 5'-TTTGAGAGTCGTTCGATTGC-3'. (SEQ ID No. 17)

DNA extracted from plasma, serum, whole blood, or tissue is subjected to polymerase chain reaction amplification with 1 picomole each of either primers APC-1 and APC-2, or primers APC-3 and APC-4 for 25 cycles at a denaturing temperature of 94° C. for 60 seconds, annealing at 51° C. for 90 seconds, and extension at 72° C. for 90 seconds each cycle. The reaction mixture consists of 1×Taq buffer, 1.5 mM $MgCl_2$, 200 micromolar dNTPs, and 1 unit Taq polymerase (Fisher, Pittsburgh, Pa.) in a volume of 50 μL. Hemi-nested PCR amplification is then performed on 5 μL of the first amplification product, wherein primers APC-1 and APC-2 are replaced with primers APC-1 and APC-5; and in a separate reaction primers APC-1 and APC-2 replaced with primers APC-2 and APC-3; and in a separate reaction primers APC-3 and APC-4 replaced with primers APC-6 and APC-4. Reaction conditions for the second round of amplification are the same as for the first, except that 10 picomoles of each primer are used, and the cycle number is 35. The PCR products are detected by agarose gel electrophoresis, bands are excised from the gel and DNA isolated using the GeneClean kit (Bio101) according to the manufacturer's instructions. DNA is then asymmetrically reamplified with one primer at 100 picomoles and the other at 2 picomoles for eventual cycle sequencing, wherein primer pairs are: APC-1 and APC-5; APC-2 and APC-3 APC-4 and APC-6. The asymmetric amplification is performed as described in McCabe (1990, *PCR Protocols. A guide to methods and applications* (Innis, Gelfand, Sninsky, & White, eds.) Academic Press, pp. 76-83) using approximately 1.4 ng of each PCR product and annealing at 51° C. Cycle sequencing is then performed as described in Brow (1990, *PCR Protocols. A guide to methods and applications* (Innis, Gelfand, Sninsky, & White, eds.) Academic Press, pp. 189-196) using the limiting primer labeled with $^{32}$P.

5-10 mL of blood was collected in an EDTA-coated siliconized glass vacutainer tube from an individual with colorectal clinically-diagnosed cancer whose tumor was known to harbor an APC mutation consisting of a five base deletion at 3961-3965. Plasma was fractionated from whole blood by centrifugation at 400×g at room temperature for ten minutes. DNA was then extracted from 200 μL of plasma using the High-Pure Viral Nucleic Acid kit (Boehringer Mannheim). The extracted DNA was initially amplified as described above using primers APC-1 and APC-7 (5'-TGCTGGATTTGGT-TCTAGGG-3'; SEQ ID No. 18), then reamplified with primers APC-7 and APC-8 (5'-TCAGACGACACAGGAAG-CAG-3'; SEQ ID No. 19) as in the hemi-nested reactions described above. The PCR products were electrophoresed through a 5% agarose gel and examined by ethidium bromide staining. The appropriate region of the gel was excised and prepped by the GeneClean, and this DNA then cycle sequenced as described above, thereby confirming an APC mutation in the plasma DNA.

Plasma from this individual having APC mutated plasma DNA was further evaluated for the presence of mutated K-ras DNA (by the method described in example 1), and mutated P53 DNA (by the method described in example 2). Plasma was negative for both mutated K-ras and mutated P53 DNA in this individual.

This example demonstrates that mutated APC DNA may be detected in blood. Further, detection of mutated APC in blood is indicative of the presence of mutated tissue, and provides a predictive risk factor for neoplastic disease. The example demonstrates that detection of mutated APC in blood is particularly advantageous in predicting for neoplastic disease of a gastrointestinal origin, and particularly a colorectal neoplastic disease.

It will be understood that enriching the extracted DNA for APC by methods as described in the invention will further increase the sensitivity of the assay for detection of mutated APC DNA in blood. It is further shown by this example that it is particularly advantageous to include methods detecting mutated APC within a multiplexed assay or an oncogene or tumor-associated nucleic acid assay panel or array, wherein it is particularly advantageous to assay blood plasma or serum for mutated APC in addition to mutated K-ras and/or mutated P53. It is well recognized that APC mutations occur early and commonly in premalignant neoplasms such as colorectal adenoma, thus it is particularly evident that it is advantageous to detect mutated APC in the blood of humans without clinically-diagnosed cancer, as to predict for premalignant disease or risk for neoplastic disease, and to further indicate the need for additional diagnostic testing including but not limited to endoscopy, colonoscopy, sigmoidoscopy, radiologic imaging, radionucleotide scanning, ultrasonography, PET scanning, or further evaluation of organ or site specific bodily fluids or stool, wherein bodily fluid includes but is not limited to that collected by drainage, aspiration, direct sampling, and lavage.

EXAMPLE 5

Detection of mutated K-ras DNA in the Plasma of a Human without Clinically-Diagnosed Cancer having a Hyperplastic Proliferative Condition Hyperplastic colorectal polyps are non-neoplastic proliferative conditions. Blood was prospectively examined from a human found upon colonoscopy and polypectomy to have a K-ras mutated hyperplastic polyp but not to have cancer. The method of examination was identical to the method provided in example 1. Mutated K-ras DNA was similarly demonstrated in the plasma from the human. This example demonstrates that the methods of the invention enable detection of mutated DNA in the blood of individuals having hyperplastic tissue harboring mutated DNA.

EXAMPLE 6

Detection of Mutated K-ras DNA in the Plasma of a Human with an In-Situ (Non-Invasive) Carcinoma In-situ carcinomas are early cancers which by definition are localized and non-invasive. A human undergoing a colonoscopy was found to have a K-ras mutated in-situ colorectal carcinoma. Plasma was prospectively obtained from the human and examined using the methods identical to those provided in example 1. Mutated K-ras DNA was similarly detected in the plasma from the human. This example demonstrates that the methods of the invention enable detection of mutated DNA in blood from humans having localized, non-invasive or pre-invasive, in-situ malignancy when the malignancy harbors mutated DNA.

EXAMPLE 7

Prophetic Examples of the Use of the Assays of the Invention

The following example is illustrative of potential clinical uses for the assays of the invention.

Case 1

A 70 year old woman with a long history of cigarette smoking visits her doctor because she is concerned about her risk of developing lung cancer. A sample of blood is drawn and plasma is prepared. An aliquot of the plasma is incubated with metal beads containing oligonucleotides complementary to exons of the TP53 tumor suppressor gene bound to their surface. The beads are drawn to the side of the tube with a magnet, and the tube is washed several times with water. The tube is then heated to release the affinity-captured TP53 DNA fragments, and the solution containing these fragments is applied to a sequencing chip useful for detecting mutations in the TP53 gene (commercially available from Affymetrix). The machine designed to read the sequencing chip detects a deletion of codon 158 of the TP53 gene. Confirmation of the presence of the TP53 mutation is obtained from a sputum sample, and it is concluded that the patient is at high risk for development of lung cancer. She is closely followed by CXR, spiral CT scan, and bronchoscopy, and the patient has blood plasma regularly monitored by a version of the invention adapted specifically for her TP53 mutation. After enrichment of the plasma for the exon carrying the codon 158 mutation using metal beads followed by amplification, a quantitative assay for the presence of the mutation is used to determine the amount of mutant present in the plasma. For one year, the patient has no detectable mutant DNA, following which a steady rise in the amount of mutant DNA is noted over six months. No clinical or radiographic evidence of disease is present at this time. The patient begins a P53-directed chemopreventive therapy and after a successful course remains free of disease while being monitored by the codon 158 assay.

This example further illustrates the use of the invention in a quantitative fashion, in this case using the affinity-capture version of the invention. A tumor suppressor gene frequently altered in lung cancer (TP53) is enriched from the plasma and used as the substrate for a quantitative portion of the invention. This mutant can then be followed and intervention begun early, when chemopreventive therapy is most effective.

This clinical vignette is meant as an example of the uses to which the invention may be put, and is not meant in any way to be limitations upon the range or type of assays or extracellular mutant DNAs detectable in the plasma or serum by the invention.

It should be understood that the foregoing disclosure emphasizes certain specific embodiments of the invention and that all modifications or alternatives equivalent thereto are within the spirit and scope of the invention as set forth in the appended claims.

We claim:

1. A method for determining an acquired predictive risk factor for a non-hematologic disease in a human without cancer having a premalignancy that is an adenoma, or non-hematopoietic dysplastic or hyperplastic cells or tissue, the method comprising the steps of:
   a. purifying extracellular nucleic acid from blood from a human without cancer to prepare extracted extracellular nucleic acid containing DNA encoding a mutated gene or fragment thereof; and concurrently or sequentially,
   b. enriching the extracted extracellular nucleic acid for the mutated gene DNA or a fragment thereof, wherein the mutated gene DNA or a fragment thereof is concentrated or isolated from the remaining extracted extracellular nucleic acid;
   c. amplifying the mutated gene DNA or a fragment thereof, or amplifying a signal from the enriched mutated DNA or a fragment thereof; and
   d. detecting the product of the amplified mutated gene DNA or the product of its amplified fragment, or the amplified signal of the mutated DNA or the amplified signal of a fragment thereof, whereby said detection determines a predictive risk factor for a nonhematologic disease in the human without cancer.

2. A method according to claim 1, wherein the product of the amplified mutated gene DNA is detected using a detection method that is gel electrophoresis, single strand conformation polymorphism, heteroduplex analysis, denaturing gradient gel electrophoresis, mismatch cleavage assay, immunological detection methods, nucleic acid hybridization, Southern blot analysis, electrochemiluminescence, reverse dot blot detection, or high-performance liquid chromatography.

3. The method of claim 1 wherein extracellular nucleic acid is purified from the plasma or serum fraction of blood.

4. The method of claim 1 wherein the enriched mutated gene DNA or a fragment thereof of subpart (b) is amplified in subpart (c) using an amplification method that is polymerase chain reaction, ligase chain reaction, boomerang DNA amplification, Q-beta replication, transcription-based amplification, isothermal nucleic acid sequence based amplification, self-sustained sequence replication assay, strand displacement activation, or cycling probe technology.

5. A method of claim 1 wherein mutated gene DNA or a fragment thereof is enriched in subpart (b) through an endonuclease-mediated restriction digestion.

6. A method of claim 1 wherein mutated gene DNA or a fragment thereof is enriched in subpart (b) by hybridization of the mutated gene DNA or a fragment thereof to an oligonucleotide to form a hybridized complex.

7. A method according to claim 6 wherein the hybridized complex is further subjected to a magnetic field.

8. A method according to claim 6 wherein the hybridized complex is further subjected to an electric field.

9. A method according to claim 6 wherein the endonuclease is BstNI, HinP1 I, or Msp I.

10. A method according to claim 1, wherein the mutated DNA encodes a mutated oncogene or fragment thereof.

11. A method according to claim 10, wherein the mutated oncogene is mutated K-ras.

12. A method according to claim 10, wherein the mutated oncogene is mutated APC.

13. A method according to claim 1, wherein the mutated DNA is DNA having a microsatellite alteration.

14. A method according to claim 1, wherein the non-hematologic disease is colorectal adenoma, cervical dysplasia, atypical squamous metaplasia of the lung, bronchial dysplasia, atypical hyperplasia of the breast, prostatic intraepithelial neoplasia, atypical endometrial hyperplasia, dysplastic nevi of the skin, or Barrett's esophagus.

15. The method of claim 1, further comprising the steps of:
  e) demonstrating that the mutated gene DNA is absent in normal cells from the human, thereby indicating that the predictive risk factor is an acquired predictive risk factor.

16. A method for enriching purified extracellular DNA for extracellular mutated DNA or a fragment thereof in blood of a human without cancer having a premalignancy that is an adenoma, or non-hematopoietic dysplastic or hyperplastic cells or tissue, the method comprising the steps of:
  a. purifying extracellular nucleic acid from blood of a human without cancer to prepare extracellular nucleic acid containing a mutated DNA species or fragment thereof, and concurrently or sequentially
  b. hybridizing an oligonucleotide that is complementary to the mutated DNA or a mutated DNA fragment to produce a hybridized product of mutated DNA or a fragment thereof; and
  c. separating the hybridized product of mutated DNA or a fragment thereof from the remaining non-hybridized extracellular nucleic acid, thereby enriching the purified extracellular DNA for the mutated DNA or a fragment thereof.

17. The method of claim 16 wherein the extracellular nucleic acid is purified from the plasma or serum fraction of blood.

18. A method according to claim 16 wherein the oligonucleotide is further bound to a non-biologic surface.

19. A method according to claim 16 wherein in subpart (c) the hybridized product is subjected to a magnetic field.

20. A method according to claim 16 wherein in subpart (c) the hybridized product is subjected to an electric field.

21. A method according to claim 16, wherein the mutated DNA is mutated oncogene DNA.

22. A method according to claim 21, wherein the mutated oncogene is mutated K-ras.

23. A method according to claim 21, wherein the mutated oncogene is mutated APC.

24. A method according to claim 21, wherein the mutated oncogene is mutated P53.

25. A method according to claim 16, wherein the mutated DNA is DNA having a microsatellite alteration.

26. A method of identifying a human having a disease or premalignancy without clinical symptoms by detecting a mutation in DNA from blood or a blood fraction from the human, wherein the mutation is an acquired mutation that is associated with the disease or premalignancy, and wherein the disease or condition is colorectal adenoma, cervical dysplasia, atypical squamous metaplasia of the lung, bronchial dysplasia, atypical hyperplasia of the breast, prostatic intraepithelial neoplasia, atypical endometrial hyperplasia, dysplastic nevi of the skin, or Barrett's esophagus; the method comprising the steps of:
  a. purifying extracellular nucleic acid from blood or a blood fraction from a human without cancer to prepare extracted extracellular nucleic acid containing said mutated DNA;
  b. amplifying the mutated DNA, or alternatively amplifying a signal from the mutated DNA; and
  c. detecting the product of the amplified mutated DNA or the amplified signal of the mutated DNA,
  wherein the human is identified as having the disease or premalignancy.

27. A method according to claim 26, wherein the evaluation of blood or a blood fraction from a human for said mutation assists in the identification of said disease or premalignant condition.

28. A method according to claim 26, wherein extracellular nucleic acid is purified from the plasma or serum fraction of blood.

29. A method according to claim 26, further comprising the step of performing a diagnostic test that is colonoscopy, sigmoidoscopy, endoscopy, bronchoscopy, radiologic imaging, ultrasonography, radionucleotide imaging, PET scanning, and evaluation of organ specific bodily fluid, stool, or lavage fluid.

30. A method according to claim 26, wherein the mutated DNA is a DNA microsatellite alteration.

31. The method of claim 26, wherein the mutated DNA of subpart (a) is amplified in subpart (b) using an amplification method that is polymerase chain reaction, ligase chain reaction, boomerang DNA amplification, Q-beta replication, transcription-based amplification, isothermal nucleic acid sequence based amplification, self-sustained sequence replication assay, strand displacement activation, or cycling probe technology.

32. The method of claim 26, wherein the product of the amplified mutated DNA is detected using a method that is gel electrophoresis, single strand conformation polymorphism, heteroduplex analysis, denaturing gradient gel electrophoresis, mismatch cleavage assay, immunological detection methods, nucleic acid hybridization, Southern blot analysis, electrochemiluminescence, reverse dot blot detection, or high-performance liquid chromatography.

33. A method according to claim 26, wherein prior to amplification in subpart (b), the mutated DNA in subpart (a) is enriched, wherein the mutated DNA is concentrated or isolated from the remaining extracted nucleic acid.

* * * * *

```
                              SEQUENCE LISTING

<160> NUMBER OF SEQ ID NOS: 19

<210> SEQ ID NO 1
<211> LENGTH: 19
<212> TYPE: DNA
<213> ORGANISM: Homo sapiens

<400> SEQUENCE: 1
gttggagctc gtggcgtag                                                    19

<210> SEQ ID NO 2
<211> LENGTH: 19
<212> TYPE: DNA
<213> ORGANISM: Homo sapiens

<400> SEQUENCE: 2
gttggagctc gtggcgtag                                                    19

<210> SEQ ID NO 3
<211> LENGTH: 19
<212> TYPE: DNA
<213> ORGANISM: Homo sapiens

<400> SEQUENCE: 3
gttggagcta gtggcgtag                                                    19

<210> SEQ ID NO 4
<211> LENGTH: 17
<212> TYPE: DNA
<213> ORGANISM: Homo sapiens

<400> SEQUENCE: 4
ccatgagcac tgctcag                                                      17

<210> SEQ ID NO 5
<211> LENGTH: 17
<212> TYPE: DNA
<213> ORGANISM: Homo sapiens

<400> SEQUENCE: 5
ccatgagctc tgctcag                                                      17

<210> SEQ ID NO 6
<211> LENGTH: 17
<212> TYPE: DNA
<213> ORGANISM: Homo sapiens

<400> SEQUENCE: 6
ccatgagccc tgctcag                                                      17
```

```
<210> SEQ ID NO 7
<211> LENGTH: 19
<212> TYPE: DNA
<213> ORGANISM: Homo sapiens

<400> SEQUENCE: 7
gcagtcacag cacatgacg                                              19

<210> SEQ ID NO 8
<211> LENGTH: 18
<212> TYPE: DNA
<213> ORGANISM: Homo sapiens

<400> SEQUENCE: 8
aatcagaggc ctggggac                                               18

<210> SEQ ID NO 9
<211> LENGTH: 20
<212> TYPE: DNA
<213> ORGANISM: Homo sapiens

<400> SEQUENCE: 9
gggccagacc taagagcaat                                             20

<210> SEQ ID NO 10
<211> LENGTH: 18
<212> TYPE: DNA
<213> ORGANISM: Homo sapiens

<400> SEQUENCE: 10
ttgggccggt gttatctc                                               18

<210> SEQ ID NO 11
<211> LENGTH: 18
<212> TYPE: DNA
<213> ORGANISM: Homo sapiens

<400> SEQUENCE: 11
atggtgcgga tgggcctc                                               18

<210> SEQ ID NO 12
<211> LENGTH: 21
<212> TYPE: DNA
<213> ORGANISM: Homo sapiens

<400> SEQUENCE: 12
tccacacctt catctaatgc c                                           21

<210> SEQ ID NO 13
<211> LENGTH: 20
<212> TYPE: DNA
<213> ORGANISM: Homo sapiens

<400> SEQUENCE: 13
cattccactg catggttcac                                             20

<210> SEQ ID NO 14
<211> LENGTH: 20
<212> TYPE: DNA
<213> ORGANISM: Homo sapiens

<400> SEQUENCE: 14
ctgaagatcc tgtgagcgaa                                             20
```

```
<210> SEQ ID NO 15
<211> LENGTH: 20
<212> TYPE: DNA
<213> ORGANISM: Homo sapiens

<400> SEQUENCE: 15
tcaggctgga tgaacaagaa                                            20

<210> SEQ ID NO 16
<211> LENGTH: 20
<212> TYPE: DNA
<213> ORGANISM: Homo sapiens

<400> SEQUENCE: 16
cttcgctcac aggatcttca                                            20

<210> SEQ ID NO 17
<211> LENGTH: 20
<212> TYPE: DNA
<213> ORGANISM: Homo sapiens

<400> SEQUENCE: 17
tttgagagtc gttcgattgc                                            20

<210> SEQ ID NO 18
<211> LENGTH: 20
<212> TYPE: DNA
<213> ORGANISM: Homo sapiens

<400> SEQUENCE: 18
tgctggattt ggttctaggg                                            20

<210> SEQ ID NO 19
<211> LENGTH: 20
<212> TYPE: DNA
<213> ORGANISM: Homo sapiens

<400> SEQUENCE: 19
tcagacgaca caggaagcag                                            20
```